(12) United States Patent
Vougioukalakis et al.

(10) Patent No.: US 12,121,581 B2
(45) Date of Patent: Oct. 22, 2024

(54) METHOD OF PHOTODYNAMIC THERAPY

(71) Applicants: OSLO UNIVERSITETSSYKEHUS HF, Oslo (NO); CONSEJO SUPERIOR DE INVESTIGACIONES CIENTÍFICAS, Madrid (ES); UNIVERSITAT POLITÉCNICA DE VALÈNCIA, Valencia (ES); National and Kapodistrian University of Athens, Athens (GR)

(72) Inventors: Georgios C. Vougioukalakis, Attica (GR); Georgios Rotas, Attica (GR); Theodossis A. Theodossiou, Oslo (NO); Kristian Berg, Heggedal (NO); Ángel Miranda Alonso Miguel, Valencia (ES)

(73) Assignees: OSLO UNIVERSITETSSYKEHUS HF, Oslo (NO); CONSEJO SUPERIOR DE INVESTIGACIONES CIENTÍFICAS, Madrid (ES); UNIVERSITAT POLITÉCNICA DE VALÈNCIA, Valencia (ES); NATIONAL AND KAPODISTRIAN UNIVERSITY OF ATHENS, Athens (GR)

( * ) Notice: Subject to any disclaimer, the term of this patent is extended or adjusted under 35 U.S.C. 154(b) by 784 days.

(21) Appl. No.: 17/254,506

(22) PCT Filed: Jun. 21, 2018

(86) PCT No.: PCT/GB2018/051744
§ 371 (c)(1),
(2) Date: Dec. 21, 2020

(87) PCT Pub. No.: WO2019/243757
PCT Pub. Date: Dec. 26, 2019

(65) Prior Publication Data
US 2021/0121570 A1 Apr. 29, 2021

(51) Int. Cl.
*A61K 41/00* (2020.01)
*A61K 47/54* (2017.01)
(Continued)

(52) U.S. Cl.
CPC ...... *A61K 41/0057* (2013.01); *A61K 41/0061* (2013.01); *A61K 47/545* (2017.08); *A61K 47/55* (2017.08); *A61P 35/00* (2018.01)

(58) Field of Classification Search
CPC .. A61K 41/0057; A61K 47/545; A61K 47/55; A61K 41/0061; A61P 35/00
See application file for complete search history.

(56) References Cited

U.S. PATENT DOCUMENTS

| 5,773,592 A | 6/1998 | Mills |
| 2014/0010760 A1 | 1/2014 | Giri et al. |
| 2017/0202966 A1 | 7/2017 | Wood et al. |

FOREIGN PATENT DOCUMENTS

| CN | 104434876 A | 3/2015 |
| JP | 2009542810 A | 12/2009 |

(Continued)

OTHER PUBLICATIONS

Yang; Chem. Soc. Rev., 2020, 49, 6800-6815. (Year: 2020).*

(Continued)

*Primary Examiner* — Daniel R Carcanague
(74) *Attorney, Agent, or Firm* — Meunier Carlin & Curfman LLC

(57) ABSTRACT

$$A\text{--}[L\text{--}B]_n]_x \quad (I)$$

Figure 1:
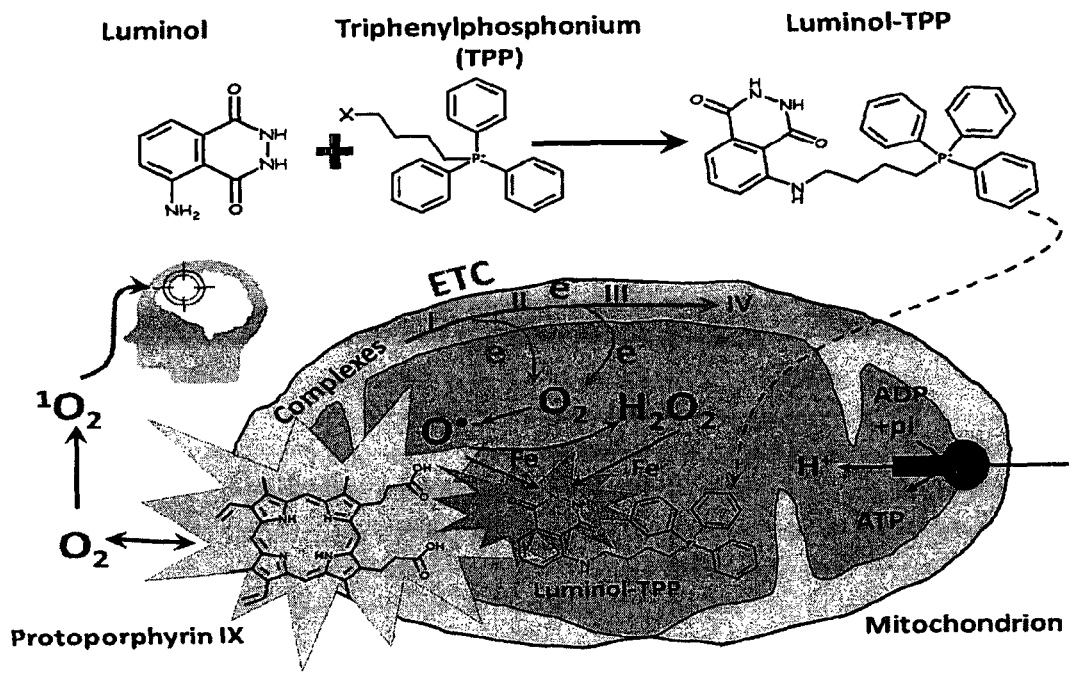

The invention provides mitochondria-targeted chemiluminescent agents and their use in methods of photodynamic therapy (PDT). In particular, the invention provides com- (Continued)

pounds of general formula (I), and their pharmaceutically acceptable salts: (I) in which A represents a chemiluminescent moiety; each L, which may be the same or different, is either a direct bond or a linker; each B, which may be the same or different, represents a mitotropic moiety; n is an integer from 1 to 3, preferably 1; and x is an integer from 1 to 3, preferably 1. Such compounds find particular use in the treatment of deeply-sited tumours, e.g. glioblastoma multiforme (GBM), when used in combination with a photosensitizer or photosensitizer precursor.

9 Claims, 12 Drawing Sheets

(51) Int. Cl.
*A61K 47/55* (2017.01)
*A61P 35/00* (2006.01)

(56) References Cited

FOREIGN PATENT DOCUMENTS

| WO | 2008008315 A | 1/2008 | | |
|---|---|---|---|---|
| WO | 2008011707 A1 | 1/2008 | | |
| WO | 2017044445 A1 | 3/2017 | | |
| WO | WO-2023041938 A1 | * | 3/2023 | ......... A61K 41/0057 |

OTHER PUBLICATIONS

Hu; Bioconjugate Chem. 2017, 28, 590-599. (Year: 2017).*
Kim; International Journal of Nanomedicine, 2013, 2173-2186. (Year: 2013).*
Laptev; British Journal of Cancer 2006, 95, 189-196. (Year: 2006).*
Liu; Chem. Commun., 2016, 52, 12330-12333. (Year: 2016).*
Mao; Chem 2017, 3, 991-1007. (Year: 2017).*
Package Insert for aminolevulinic acid hydrochloride dated Jun. 2017. (Year: 2017).*
Pantelia; Molecules 2019, 24, 3957. (Year: 2019).*
Stepp; Lasers in Surgery and Medicine 2018, 50, 399-419. (Year: 2018).*
Zielonka; Chem. Rev. 2017, 117, 15, 10043-10120. (Year: 2017).*
Kang; Biomater Res 2018, 22, 34. (Year: 2018).*
Office action issued for Japanese Patent Application No. 2021-520472, dated Jul. 6, 2022.
Office action issued for Japanese Patent Application No. 2021-520472, dated Mar. 29, 2023.
Xu, et al., "Enhanced Photodynamic Efficiency Achieved via a Dual-Targeted Strategy Based on Photosensitizer/Micelle Structure," Biomacromolecules, 15, 4249-4259; dated Oct. 20, 2014; 6 pages.
Lei, et al., "Mitochondria-targeting properties and photodynamic activities of porphyrin derivatives bearing cationic pendant," Journal of Photochemistry and Photobiology B: Biology, 98, 2010, 167-171; dated Dec. 22, 2009; 6 pages.
Bancirova, et al., "The photodynamic effect: the comparison of chemiexcitation by luminol and phthalhydrazide," Luminescence, 2011, 26(6): 410-415; dated Sep. 20, 2010; 8 pages.
Yuan, et al., "Chemical Molecule-Induced Light-Activated System for Anticancer and Antifungal Activites," Journal of the America Chemical Society, 134, 2012, 13184-13187; dated Jul. 25, 2012; 4 pages.
Zhang, et al., "Small Molecule-Initiated Light-Activated Semiconducting Polymer Dots: An Integrated Nanoplatform for Targeted Photodynamic Therapy and Imaging of Cancer Cells," Analytical Chemistry, 86, 2014, 3092-3099; dated Feb. 19, 2014; 8 pages.
Nakonechny, et al., "Intracellular Antimicrobial Photodynamic Therapy: A Novel Technique for Efficient Eradication of Pathogenic Bacteria," Photochemistry and Photobiology, 86, 2010, 1350-1355; dated Aug. 12, 2010; 8 pages.
Magalhaes, et al., "Chemiluminescence and Bioluminescence as a Excitation Source in the Photodynamic Therapy of Caner: A Critical Review," ChemPhysChem, 2016, 17(15), 2286-2294; dated May 25, 2016; 10 pages.
Rosania, "Supertargeted Chemistry: Identifying Relationships Between Molecular Structures and their Sub-Cellular Distribution," Current Topics in Medicinal Chemistry, 2003, 3(6), 659-685; 27 pages.
Theodossiou, et al., "A novel mitotropic oligolsyine nanocarrier: Target delivery of covalently bound D-Luciferin to cell mitochondria," Mitochondrion, 11(6), 2011 982-986; dated Aug. 11, 2011; 6 pages.
Search Report issued in GB application No. GB1607271.2; dated Feb. 13, 2017; 8 pages.
International Search Report issued in International Application No. PCT/GB2018/051744; dated Mar. 20, 2019; 17 pages.
International Preliminary Report on Patentability issued in International Application No. PCT/GB2018/051744; dated Dec. 22, 2020; 9 pages.

* cited by examiner

METHOD OF PHOTODYNAMIC THERAPY

TECHNICAL FIELD

The present invention relates to improvements in and relating to methods of photodynamic therapy (PDT) and, in particular, to such methods for the targeted treatment of diseases and conditions characterised by hyperproliferative and/or abnormal cells, without the need for an external light source. More specifically, the invention relates to such methods for the treatment of tumours, especially those which are inaccessible when using existing PDT methods.

The invention further relates to novel chemiluminescent agents having mitochondrial affinity, to methods for their preparation and to their use as an intracellular light source in methods of PDT which employ a photosensitizer or photosensitizer precursor.

BACKGROUND OF THE INVENTION

Conventional treatment of internal tumours typically involves invasive surgery, radiotherapy, non-curative chemotherapy, or a combination of these. Intracranial tumours such as glioblastoma multiforme (GBM) are one example of deeply-sited tumours which are very difficult to treat because of their location and highly aggressive characteristics.

Approximately 28,000 new cases of malignant glioma such as GBM are diagnosed every year in the EU and the US and in 240,000 patients globally every year. The current standard therapy consists of highly invasive (open brain) surgery which removes about 99% of the tumour but leaves behind about a billion cells, leading to recurrence. Radiotherapy may be used as an adjuvant to surgery (at 60-65 Gy) and together with surgery may reduce the cancer cells left behind to several million, however radiotherapy does not have a major effect on cancers such as GBM which tend to spread in several locations also harbouring radio-resistant cancer cells. Furthermore, radiotherapy is not specific in destroying cancerous vs. normal tissues. Chemotherapy with temozolomide in addition to radiotherapy may also be used. However, these therapies offer limited overall patient survival and do not produce a curative outcome these are mainly cytostatic as cells will eventually (within approx. 1 year of treatment) develop resistance and render the treatment no longer effective. The combination of surgery with radiotherapy increases the median of survival from 4.5 months (untreated) to 12.1 months. Additional chemotherapy with temozolomide extends survival to 14.6 months. The relative survival rate for adults diagnosed with GBM is less than 30% within one year of diagnosis and only 3% of patients live longer than five years after initial diagnosis.

Deep lying, hard to reach tumours such as GBM thus remain very difficult to treat and existing therapies offer only a minimal increase in survival rates. Therefore, the development of more targeted and less invasive therapeutic approaches with improved efficacy is urgently required.

Other methods known for use in the treatment of tumours include PDT. PDT involves the administration of a photosensitizer, either locally or systemically, followed by exposure of the affected area to photoactivating light which interacts with the ambient oxygen to produce cytotoxic intermediates. This results in the destruction of cells and the shutdown of the tumour vasculature.

PDT provides cancer treatment through the synergy of three essential, yet individually non-chemotoxic, components: (i) the photosensitizer (PS), a light activated drug; (ii) light of the appropriate wavelength to activate the PS; and (iii) the presence of oxygen, which is the terminal generator of toxic species. The anti-tumour effects of PDT can mainly be categorized into three interrelated effects: (i) direct cytotoxic action which is mainly effected through either a type I or type II mechanism—the former generates reactive oxygen species (ROS) and ultimately hydroxyl radicals while a type II mechanism, prominent in the majority of PSs, generates deleterious singlet oxygen [$O_2$ ($^1\Delta_g$) or $^1O_2$]; (ii) damage to tumour vasculature; and (iii) induction of an inflammatory reaction that can lead to the development of systemic immunity, as a consequence of PDT-induced oxidative stress.

Photosensitizing agents which are currently approved for use in methods of photodynamic therapy and diagnosis include protoporphyrin IX (PpIX) which is produced from its biosynthetic non-photosensitive precursor 5-aminolevulinic acid (5-ALA). Following the external administration of 5-ALA, the biosynthetic cycle of heme facilitates its conversion to the active photosensitizer PpIX in cell mitochondria. Cancer cells treated with 5-ALA accumulate larger amounts of PpIX mainly due to their higher amount of porphobilinogen deaminase and/or substantially lower amount of ferrochelatase (this enzyme catalyses the chelation of iron by PpIX in the mitochondrial matrix to produce heme which is then transported out of the mitochondria). On subsequent exposure to light, PpIX is excited from its ground singlet state to its excited singlet state. It then undergoes intersystem crossing to a longer-lived excited triplet state. Upon interaction of the PpIX in the triplet state with an oxygen molecule (in the ground triplet state), an energy transfer takes place from the PpIX to oxygen. This results in a mutual spin flip of the two molecules which allows the PpIX to relax back to its ground singlet state, whilst creating an excited singlet state oxygen molecule which is cytotoxic.

Photosensitizing agents are also known for use in methods of photodynamic diagnosis of cancerous cells and tissues and can also be used to guide surgical resection of tumour masses. For example, PDT is used as an aid to surgery in the treatment of bladder cancer. 5-ALA induced PpIX fluorescence is currently also used intraoperatively for fluorescence guided resection in the treatment of GBIM (see Stummer et al., Lancet Oncol., 2006, 7(5): 392-401). However, due to limitations of conventional PDT procedures (e.g. light accessibility and light penetration into tissue) it cannot at present be used to treat this aggressive condition without the need for surgical intervention.

The main limitations of existing methods of PDT as an anti-cancer treatment are poor determination of the treated area by the clinician, poor definition of treated tumour volume, and the limited depth of penetration of the photoactivating light in tissue (1.5 cm). This leads to ineffective treatment and viable cancer cells being left behind. 5-ALA based PDT, for example, is highly specific and efficient for the treatment of actinic keratosis and basal cell carcinoma with a high cure rate, but only for lesions thinner than 2 mm. For thicker lesions or non-superficial cancers, 5-ALA PDT cannot guarantee the patient a cure, and in cases of large tumours it is merely palliative. This is due to the limited tissue penetration of light at the wavelength of PpIX activation (635 nm).

Whilst in some cases PDT may be used to treat deeper sited target cells in solid organs or hollow organs like the oesophagus, this generally involves the use of a device, such as a catheter- or endoscope-directed fibre optic, for light activation of the photosensitizer. Not only is this a complicated procedure, but it precludes access to certain areas of the body and introduces a level of invasiveness to the treatment. It also cannot eradicate the entirety of the cancer cells, and cannot be applied to multi-foci diseases (e.g. gliomas) or multi-foci metastases. Thus, although appropriate for treating superficial tumours, the use of existing PDT methods in treating deeply seated tumour cells and anatomically less accessible lesions is severely limited.

Since the main limitation of PDT is the access of light to the cancerous lesions, especially when these are in deep lying organs like the brain, liver or pancreas, several efforts have been made to utilise bio- or chemi-luminescence as intracellular sources which would provide the light needed for a photodynamic cell suicide following administration of the photosensitizer. One such treatment, initially developed in 2003, is BLADe (BioLuminescence Activated Destruction). BLADe relies on the intracellular transfection with the firefly luciferase enzyme and the subsequent administration of a photosensitizer and luciferin, the natural substrate of luciferase. The main shortcomings of this method are the requirement for co-localisation of the above three factors and ATP, and the need for genetic modification of the cells to produce luciferase. Also this co-localisation has to be in the very close vicinity of vulnerable, intracellular singlet oxygen targets.

Several attempts to exploit luminescence in order to achieve the desirable PDT effect have since been made (see, for example, Hsu et al., Biomaterials, 2013, 34(4): 1204-12; and Baacirova et al., Luminescence, 2011, 26(6): 410-5). Laptev et al. (Br. J. Cancer, 2006. 95(2): 189-96) have previously proposed the use of luminol together with transferrin-haematoporphyrin conjugates to kill cells by intracellular luminescence. Although they provided sufficient proof-of-concept (95% cytotoxicity), the following shortcomings are associated with these methods making them non-viable in the clinic: (i) non-specific intracellular targeting; (ii) in the work by Laptev et al., the need for transferrin as the iron source; and (iii) the lack of design for proximity to intracellular ROS.

The present invention addresses these problems and provides a clinically effective, non-invasive method of PDT. This finds use in the treatment of all tumour types and any conditions which involve hyperproliferation of cells, but is particularly suitable for the treatment of internal tumour masses which cannot be accessed using conventional PDT techniques.

SUMMARY OF THE INVENTION

The inventors now propose a method of PDT which involves the combined use of a photosensitizer, or a precursor of a photosensitizer (e.g. 5-ALA), and a chemiluminescent agent which has a profound mitochondrial affinity. This PDT method is generally referred to herein as "LUMIBLAST".

Mitochondrial affinity is achieved by the use of a "modified" chemiluminescent agent, specifically a chemiluminescent agent 'conjugate' in which at least one chemiluminescent moiety is bound to one or more mitochondria-targeting moieties (herein also referred to as "mitotropic moieties" or "mitotropic agents").

One example of a chemiluminescent agent 'conjugate' is chemically modified luminol. Chemical modification of luminol involves the attachment of chemical groups which target it to cell mitochondria and which efficiently transport it across the mitochondrial membrane. The cell mitochondria provide the reactive oxygen species and transition metal catalysts necessary for luminol luminescence. Moreover, PpIX is biosynthesised in mitochondria and is thus in close proximity to the luminol for efficient activation and deleterious singlet oxygen production. Other mitochondria-localising photosensitizers other than PpIX can also be used, especially for brain tumours where the destruction of the blood-brain barrier at the cancer site will help them accumulate selectively in the cancer lesion even at a ratio of 30:1.

Although not wishing to be bound by theory, the chemically modified luminol ('mitotropic luminol') is believed to employ the ROS generated as a result of mitochondrial respiration. Sub-cytocidal reactive oxygen species are produced by electrons leaking from the Electron Transport Chain (ETC) which reduce molecular oxygen to superoxide anion which is further dismutated to hydrogen peroxide. These low lethality ROS can generate blue luminescence ($\lambda_{max}$=420 nm) upon activation of luminol. The mitochondrial hemes or iron-sulphur centre enzymes can potentially facilitate the iron catalysis required to produce the chemiluminescence. Luminol luminescence is compatible with the PpIX Soret absorption band peaking at 405 nm and therefore it is believed to excite PpIX in situ at the mitochondria, which consequently produce deleterious singlet oxygen, killing the host cells. In this way, the mitochondrial ROS which do not pose an immediate threat to cell survival, are "upgraded" to a highly cytotoxic ROS, i.e. singlet oxygen which inflicts fatal cell damage from within the cell. This action is specific to the cancerous lesion due to the production of high levels of PpIX at the target site. This concept is illustrated in FIG. 1 in which a modified version of luminol is employed as a self-sustained, intracellular source of light and the target cell mitochondria are used as the power supply for "switching on the light". This consequently activates the cytotoxic activity of the photosensitizer (e.g. PpIX) within the tumour cells. Although this theoretical mechanism of action is described with specific reference to the chemiluminescent agent, luminol, and 5-ALA derived PpIX as the photosensitizer, as will be discussed herein other chemiluminescent agents and other photosensitizers may also be employed in the invention.

Broadly speaking, the invention thus involves the modification of known chemiluminescent agents, for example luminol, such that these are mitochondria-targeted to carry out PDT specifically on hyperproliferative and/or abnormal cells, e.g. cancer cells. As a result of this modification, the luminescence required to activate the photosensitizer at the target site is 'automatic' and even more intense in cancer cells which, in many cases, exhibit higher mitochondrial ROS formation.

For example, 5-ALA derived PpIX formation is highly specific to the cancerous GBM lesion. This high specificity leads to the possibility of a GBM treatment where no invasive approach is required, but just the systemic administration of a mitotropic chemiluminescent agent, such as "mitotropic-luminol", and 5-ALA is sufficient to eradicate all GMB lesions in the brain. This is especially important since GBM is highly migratory within the brain following its initial occurrence and resurfaces at different brain locations. When used to treat GBM, the invention also takes advantage of the GBM-induced destruction of the blood-brain barrier so that both the modified chemiluminescent agent (e.g. luminol) and the photosensitizer or precursor thereof (e.g. 5-ALA) reach the GMB lesions in the brain efficiently.

In the invention, PDT is effectively applied to each individual tumour cell (i.e. the PDT effect is at the single cell level, rather than the collective lesion) without the requirement for an external light source, such as a lamp or a laser which is conventionally used in PDT. This novel therapeutic approach represents a paradigm shift in PDT in which the depth of light penetration into tissue is no longer a limitation. It establishes the basis for an innovative treatment of cancer which, despite being photochemical, involves the administration of two individually non-chemotherapeutic drugs. As such, it can be repeated multiple times without the risk of adverse side-effects—this minimises the risk of metastasis and maximises the curative potential of the treatment.

The invention further addresses the need for an effective treatment of internal cancers, such as GBM, which at present are practically incurable due to their location and highly aggressive nature, without the need for invasive surgery, ionizing radiation or non-curative chemotherapy. Such treatment may be either as a primary treatment and/or as a photochemotherapeutic which is able to effectively control the progression of the disease for life through repeated, non-invasive, treatments. This novel approach to the treatment of inaccessible cancers extends to the treatment of other diseases and conditions which are characterised by hyperproliferative and/or abnormal cells, and, in particular, to the treatment of other cancers including those which are shallow or superficial.

DETAILED DESCRIPTION OF THE INVENTION

Definitions

As used herein, the term "chemiluminescent agent" is intended to encompass any of a variety of agents which are capable of emitting light as a result of a chemical reaction which takes place within the cell mitochondria, i.e. any agent which can be 'activated' once localised in the mitochondria. More specifically, the chemiluminescent agent will be an agent which emits light following reaction with a substance which is either present in cell mitochondria or which is generated therein, such as a reactive oxygen or nitrogen species. Such oxygen species include, for example, any reactive oxygen species (ROS) such as oxygen radicals, oxygen superoxide anion, hydroxyl radicals, etc., and hydrogen peroxide. Nitrogen species include, for example, nitric oxide, peroxynitrite, nitrogen oxides, etc. As will be understood, any chemiluminescent agent for use in the invention will be physiologically tolerable.

As used herein, the term "chemiluminescent moiety" encompasses any chemiluminescent agent or any moiety derived from a chemiluminescent agent, i.e. a derivative thereof Any derivative should retain the light-emitting properties of the parent molecule as noted above. This should similarly meet the requirement of physiological tolerability in vivo. Examples of derivatives include chemiluminescent agents carrying one or more additional functional or non-functional groups (e.g. substituents). The term "derivative" also extends to a fragment or residue of a chemiluminescent agent.

As used herein, the term "nitotropic moiety" is intended to encompass any physiologically acceptable agent which is capable of targeting and accumulating in the mitochondria. It also encompasses derivatives of mitotropic agents which retain the mitochondria-targeting properties of the parent molecule. The term "derivative" extends to a fragment or residue of a mitotropic agent.

As used herein, the term "photosensitizer precursor" is intended to encompass any compound which is converted metabolically to a photosensitizer and is thus essentially equivalent thereto.

The term "pharmaceutically acceptable salt" as used herein refers to any pharmaceutically acceptable organic or inorganic salt of any of the compounds herein described. A pharmaceutically acceptable salt may include one or more additional molecules such as counter-ions. The counter-ions may be any organic or inorganic group which stabilizes the charge on the parent compound. If the compound is a base, a suitable pharmaceutically acceptable salt may be prepared by reaction of the free base with an organic or inorganic acid. If the compound is an acid, a suitable pharmaceutically acceptable salt may be prepared by reaction of the free acid with an organic or inorganic base.

The term "pharmaceutically acceptable" means that the compound or composition is chemically and/or toxicologically compatible with other components of the formulation or with the patient (e.g. human) to be treated.

By "a pharmaceutical composition" is meant a composition in any form suitable to be used for a medical purpose.

As used herein, the term "treatment" includes any therapeutic application that can benefit a human or non-human animal (e.g. a non-human mammal). Both human and veterinary treatments are within the scope of the present invention, although primarily the invention is aimed at the treatment of humans. The term "treatment" or "therapy" encompasses curative as well as prophylactic treatment or therapy.

The term "alkyl" as used herein refers to a monovalent saturated, linear or branched, carbon chain. Examples of alkyl groups include, but are not limited to, methyl, ethyl, n-propyl, iso-propyl, n-butyl, iso-butyl, sec-butyl, tert-butyl, n-pentyl, iso-pentyl, neo-pentyl, n-hexyl, etc. An alkyl group preferably contains from 1-6 carbon atoms, e.g. 1-4 carbon atoms.

The term "alkoxy" as used herein refers to an —O-alkyl group, wherein alkyl is as defined herein. Examples of alkoxy groups include, but are not limited to, methoxy, ethoxy, propyloxy, etc.

The term "aryl" as used herein refers to aromatic ring systems. Such ring systems contain at least one unsaturated aromatic ring. A preferred aryl group is phenyl. Unless stated otherwise, any aryl group may be substituted by one or more substituents selected from hydroxy, $C_{1-6}$ alkyl, $C_{1-6}$ alkoxy, amino, cyano, and nitro groups, or halogen atoms (e.g. F, Cl or Br). Where more than one substituent group is present, these may be the same or different.

The term "cycloalkyl" refers to a monovalent, saturated cyclic carbon system. Monocyclic cycloalkyl rings may contain from 3 to 8 carbon atoms and examples include, but are not limited to, cyclopropyl, cyclobutyl, cyclopentyl, and cyclohexyl. Unless otherwise specified, any cycloalkyl group may be substituted in one or more positions with a suitable substituent.

Where more than one substituent group is present, these may be the same or different. Suitable substituents include hydroxy, $C_{1-6}$ alkyl, $C_{1-6}$ alkoxy, amino, cyano, and nitro groups, or halogen atoms (e.g. F, Cl or Br).

The term "halogen atom" refers to —F, —Cl, —Br or —I.

The term "heterocyclic ring" as used herein refers to a saturated or partially unsaturated, 4- to 6-membered (preferably 5- or 6-membered) carbocyclic system in which at least one ring atom is a heteroatom selected from nitrogen, oxygen and sulfur, the remaining ring atoms being carbon. The heterocyclic ring structure may be linked to the remainder of the molecule through a carbon atom or through a nitrogen atom. Unless otherwise stated, any heterocyclic ring mentioned herein may optionally be substituted by one or more groups, which may be identical or different, for example hydroxy, $C_{1-6}$ alkyl, $C_{1-6}$ alkoxy, amino, cyano, or nitro groups, or halogen atoms (e.g. F, Cl or Br).

As used herein, the term "heteroaryl" refers to heterocyclic aromatic groups. Where these are monocyclic, these comprise 5- or 6-membered rings which contain at least one heteroatom selected from nitrogen, oxygen and sulfur and contain sufficient conjugated bonds to form an aromatic system. Unless otherwise stated, any heteroaryl ring mentioned herein may optionally be substituted by one or more groups, which may be identical or different, for example hydroxy, $C_{1-6}$ alkyl, $C_{1-6}$ alkoxy, amino, cyano, or nitro groups, or halogen atoms (e.g. F, Cl or Br).

Unless otherwise stated, all substituents are independent of one another.

In the case where a subscript is the integer 0 (i.e. zero), it is intended that the group to which the subscript refers is absent, i.e. there is a direct bond between the groups either side of that particular group.

In one aspect the invention provides a mitochondria-targeted chemiluminescent agent (also referred to herein as a "mitotropic chemiluminescent agent") for use in a method of photodynamic therapy.

In one embodiment the mitochondria-targeted chemiluminescent agent for use in the invention is a chemiluminescent agent 'conjugate' which comprises at least one chemiluminescent moiety attached to or otherwise associated with at least one mitotropic moiety that selectively targets mitochondria. Where this conjugate comprises more than one chemiluminescent moiety, these may be the same or different. Generally, however, these will be identical. Where the chemiluminescent moiety is attached to more than one mitotropic moiety, the mitotropic moieties may be the same or different, but preferably will be the same. In one embodiment, the conjugate comprises a single chemiluminescent moiety attached to or otherwise associated with a single mitotropic moiety.

The chemiluminescent moiety (or moieties) may be attached to the mitotropic moiety (or mitotropic moieties) through covalent or non-covalent means. It may, for example, be bound via electrostatic interaction, van der Waals forces and/or hydrogen bonding. Typically, the chemiluminescent moiety (or moieties) and mitotropic moiety (or moieties) will be covalently bound to one another, for example via one or more covalent bonds. In some cases, the chemiluminescent moiety (or moieties) may be covalently bound to the (or each) mitotropic moiety via a linking group (or "spacer").

The chemiluminescent agent 'conjugate' for use in the invention may be a compound having the following general formula (I), or a pharmaceutically acceptable salt thereof.

(I)

in which A represents a chemiluminescent moiety;
each L, which may be the same or different, is either a direct bond or a linker;
each B, which may be the same or different, represents a mitotropic moiety;
n is an integer from 1 to 3, preferably 1; and
x is an integer from 1 to 3, preferably 1.

In one embodiment of formula (I), both n and x are 1. The chemiluminescent agent 'conjugate' for use in the invention may therefore be a compound of formula (II), or a pharmaceutically acceptable salt thereof:

(II)

in which A, L and B are as herein defined.

Chemiluminescent agents suitable for use in the invention are known in the art and include, for example, luminol, isoluminol, lucigenin, acridinium esters, oxalate esters, and known analogues and derivatives thereof. Any known chemiluminescent protein or a derivative thereof may also be used. Chemiluminescent moieties for use in the invention may be 'derived' from any of these agents. Suitable derivatives may include one or more additional functional or non-functional groups (e.g. substituents), or these may comprise a fragment or residue of such agents which retain their chemiluminescent activity.

Preferred for use in the invention are chemiluminescent moieties which are derived from luminol, isoluminol, and acridinium esters. Such compounds may be substituted by one or more additional substituents, for example $C_{1-6}$ alkyl, $C_{1-6}$ alkoxy, amino, cyano, and nitro groups, or halogen atoms. For example, the phenyl ring in luminol or isoluminol may be substituted by one or more (e.g. one or two) groups selected from halogen atoms, and $C_{1-6}$ alkyl groups.

As will be understood, in order to bind to the mitotropic agent (or mitotropic agents) via a covalent bond or linker, the chemiluminescent moiety will typically be a "derivative" of the parent chemiluminescent agent. For example, this may be devoid of one or more terminal atoms or groups following formation of a covalent bond either to the linker or directly to the mitotropic agent and thus be considered a "residue" of the original molecule. For example, in the case of luminol the primary amine group may form the point of attachment either to the linker or the mitotropic moiety and so it is 'derivatised' by the loss of a single hydrogen atom, i.e. —$NH_2$ to —NH—. Other forms of derivatisation may be envisaged, including the introduction of functional groups which may react to form a covalent bond with the mitotropic agent (or agents). The particular form of 'derivatisation' required for any given chemiluminescent agent will be dependent on its structure and can readily be determined by any skilled chemist.

In formula (I) or (II), the chemiluminescent moiety may be selected from the following structures (in which * denotes its point (or points) of attachment to a linker, L, or directly to a mitotropic agent):

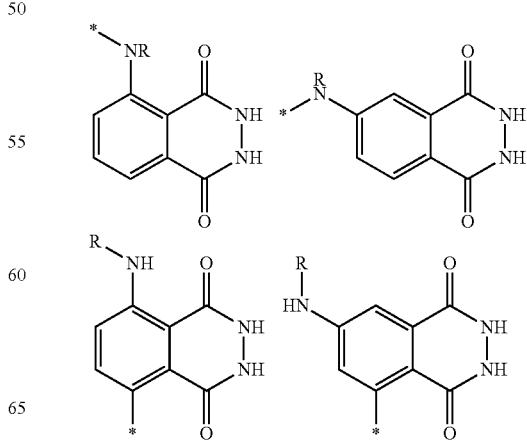

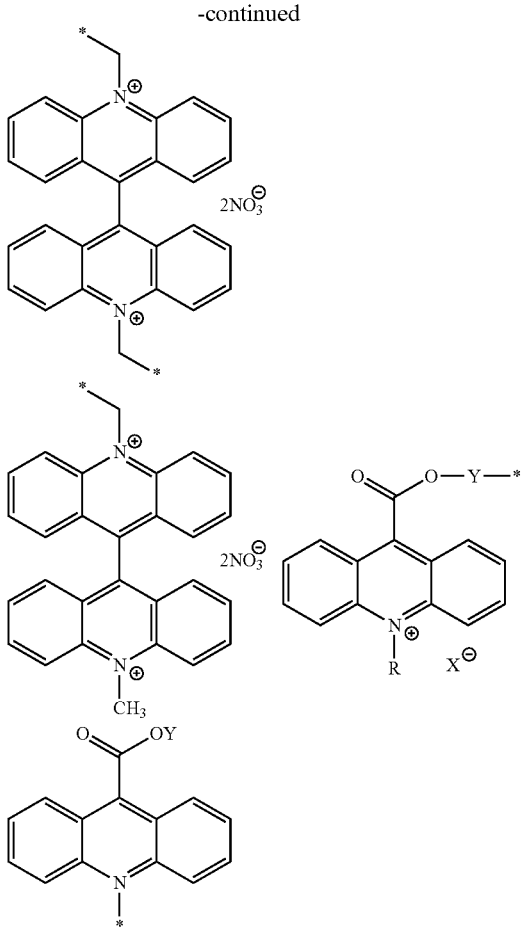

(in which each R is hydrogen, or an alkyl group such as $C_{1-3}$ alkyl (e.g. methyl);

X is a monovalent anion, e.g a Cl, Br, I, OTos, $ClO_4$, $NO_3$, $PF_6$, or $BF_4$ anion; and Y is an optionally substituted aryl (or arylene) group, e.g. optionally substituted phenyl (or phenylene)).

Where Y is a substituted aryl or arylene group, examples of suitable substituents include one or more halogen atoms (e.g. F, Cl, Br, I), $C_{1-6}$ alkyl (e.g. tert.butyl, propyl, ethyl or methyl), —$COOC_{1-6}$ alkyl (e.g. —$COOCH_3$), nitro or cyano groups.

Suitable mitotropic moieties include lipophilic moieties due to their ability to traverse the mitochondrial membrane. Moieties which have a delocalised cationic charge are also particularly suitable. Lipophilic cations are particularly suitable, especially those in which the cationic charge is delocalised. Delocalisation of charge may, for example, be provided by aromatic systems having extensive conjugation, e.g. fused ring structures, and/or the presence of multiple cationic centres distributed throughout the molecule. In the case of triphenylphosphonium, for example, the charge on the central phosphor cation is shared by the three phenyl groups.

Examples of mitotropic agents which may be used in the invention include phosphonium ions, dequalinium and dequalinium derivatives, guanidinium and guanidinium derivatives, Rhodamine 123, Rhodamine 110, triphenylethylene moieties (e.g. tamoxifen and derivatives), and 2,6-bis (4-aminophenyl)-4-[4-(dimethylamino)phenyl]thiopyrylium chloride. Any other known mitotropic agents may also be used and suitable compounds may be selected by those skilled in the art. Preferred for use in the invention are mitotropic agents selected from phosphonium ions, Rhodamine 123, and Rhodamine 110.

As will be understood, in order to bind to the chemiluminescent moiety (or chemiluminescent moieties) via a covalent bond or linker, the mitotropic agent may, in some cases, be a 'derivative' of the parent mitotropic agent. For example, this may be devoid of one or more terminal atoms or groups following formation of a covalent bond either to the linker or directly to the chemiluminescent agent (or agents) and thus be considered a"residue" of the original molecule. The particular form of 'derivatisation' required for any given mitotropic agent will be dependent on its structure and can readily be determined by any skilled chemist.

Examples of mitotropic agents for use in the invention include the following:

(in which each $R^1$, which may be the same or different (preferably the same), may for example be selected from the following:

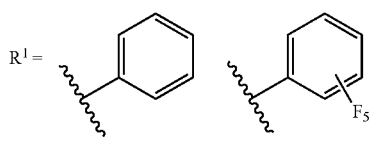

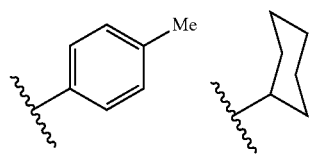

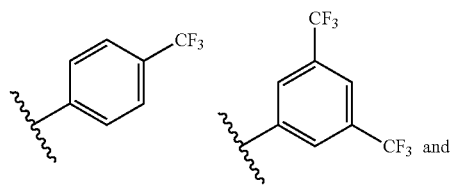

X is a monovalent anion, e.g. a Cl, Br, I, OTos, $ClO_4$, $NO_3$, $PF_6$, or $BF_4$ anion).

Other examples of mitotropic agents suitable for use in the invention include the following (in which * denotes its point of attachment to a linker, L, or directly to a chemiluminescent agent):

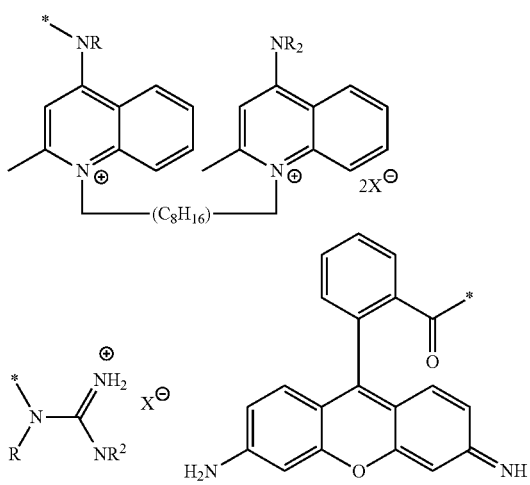

(in which each R is independently selected from hydrogen and alkyl such as $C_{1-6}$ alkyl (e.g. $C_{1-3}$ alkyl such as methyl or ethyl); and each X is independently a monovalent anion, e.g. a Cl, Br, I, OTos, $ClO_4$, $NO_3$, $PF_6$, or $BF_4$ anion).

Phosphonium ions which may be used as the mitotropic moiety include lipophilic phosphonium cations such as triphenyl phosphonium, tricyclohexyl phosphonium and perfluorinated derivatives thereof, e.g. tris-pentafluorophenyl phosphonium. In one example described herein, the chemical modification of luminol is tailor-designed to be accomplished through the addition of the mitochondria-bound, lipophilic triphenylphoshonium cation (TPP) to the primary amine of luminol through a series of different linkers (e.g. variable length alkylene chains), to produce luminol-TPPs. This family of compounds, due to their delocalised cationic charge, are expected to be taken up preferentially by cancer cells due to their hyperpolarised membranes.

In general formulae (I) and (II) above, the precise nature of the linker, L, is not considered to be critical to performance of the invention provided that this serves its intended function of linking the chemiluminescent moiety to the mitotropic moiety (or moieties) and thus enables the targeted delivery of the chemiluminescent moiety to the mitochondria. The linker may be rigid or flexible and may be cleavable in vivo at the desired target site (e.g. it may be photocleavable). Generally, it will comprise organic groups.

The linking group, L, may be hydrophilic or hydrophobic in nature. It may either be branched (including dendritic) or straight-chained, but preferably it will be straight-chained. Where the linking group is branched this may, for example, carry more than one mitotropic moiety. The linking group may be aliphatic and/or aromatic and may comprise one or more cycloalkyl, heterocyclic, aryl, or heteroaryl rings. The linking group may thus be aliphatic, (poly)cyclic and/or (poly)aromatic in nature.

The chain length of the linker may vary, although in general this may comprise a backbone containing from 1 to 20 atoms (e.g. 1 to 20 carbon atoms), preferably from 2 to 15, e.g. from 2 to 12 atoms.

Linker L may, for example, comprise an alkylene chain (preferably a $C_{1-5}$ alkylene, e.g. a $C_{2-11}$ alkylene) optionally substituted by one or more groups selected from $C_{1-3}$ alkyl, —$O(C_{1-3})$alkyl, —OH, cycloalkyl and aryl groups; and in which one or more —$CH_2$— groups of the alkylene chain may be replaced by a group independently selected from —O—, —CO—, —NR— (where R is H or $C_6$ alkyl, preferably $C_{1-3}$ alkyl, e.g. methyl), cycloalkyl, heterocyclic, aryl and heteroaryl groups.

Suitable linker groups may readily be determined by those skilled in the art. Examples of suitable linkers include optionally substituted alkylene groups, preferably unsubstituted, straight-chained alkylene groups, e.g. —$C_3H_6$—, —$C_4H_8$—, —$C_6H_{12}$—, —$C_8H_{16}$—, —$C_{10}H_{20}$—, and —$C_{11}H_{22}$—.

In cases where one or more —$CH_2$— groups of the alkylene chain are replaced by a group, these may be replaced by either —O— or —CO— groups, or by a heterocyclic ring (e.g. a saturated heterocyclic ring such as a piperazinylene group), or an aryl ring (e.g. phenylene). Examples of such linkers in which one or more —CO— are present include —CO—$CH_2$—, —CO—$C_3H_6$, —CO—$C_5H_{10}$—, —CO—$C_6H_{12}$—, and —CO—$C_{10}H_{20}$—. Other examples of suitable linkers in which two or more —O— groups are present include oligo- or poly-ethylene glycol groups, preferably polyethylene glycol groups containing from 1 to 4 ethylene oxide units, e.g. 2 or 4 ethylene oxide units.

Examples of other suitable linkers include (in the following groups either end of the linker may be attached to the chemiluminescent moiety):

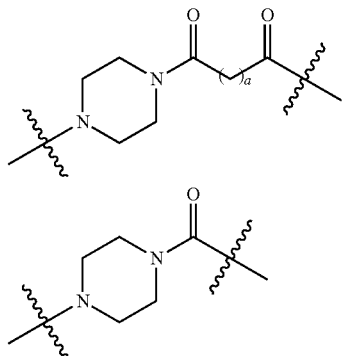

where a is an integer from 1 to 6, e.g. from 2 to 5.

In certain embodiments, the chemiluminescent agent conjugate for use in the invention is a compound of formula (III), or a pharmaceutically acceptable salt thereof:

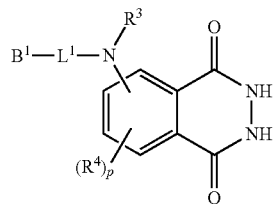

(III)

where $L^1$ is any linker as herein described;
$B^1$ is any mitotropic agent as herein described;
$R^3$ is hydrogen, or an alkyl group such as $C_{1-3}$ alkyl (e.g. methyl); and
each $R^4$ is independently selected from $C_{1-6}$ alkyl, and —$NR^5R^6$;
$R^5$ and $R^6$ are independently selected from H and $C_{1-6}$ alkyl, preferably from H and $C_{1-3}$ alkyl (e.g. —$CH_3$); and
p is an integer from 0 to 3, preferably 0, 1 or 2, e.g. 0 or 1.

Preferred compounds of formula (III) include the following compounds of formula (IIIa) and (IIIb):

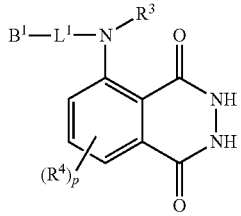
(IIIa)

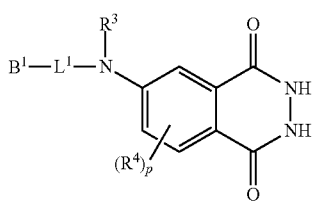
(IIIb)

where $L^1$, $B^1$, $R^3$, $R^4$ and p are as herein defined.

In formula (III), (IIIa) and (IIIb), L is preferably selected from one of the following:

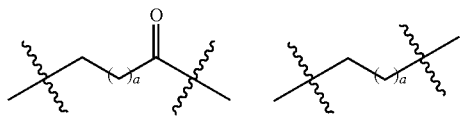

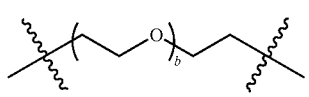

where a is an integer from 1 to 10, preferably from 3 to 10; and b is an integer from 1 to 4, e.g. 2.

In one embodiment of formula (III), (IIIa) or (IIIb), $B^1$ may be the following group:

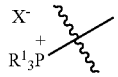

where $R^1$ is as herein defined, e.g. phenyl, toluene (e.g. o-toluene, m-toluene or p-toluene), or cyclohexyl and X is a monovalent anion, e.g. a Cl Br, or I anion).

In certain embodiments, the chemiluminescent agent conjugate for use in the invention is a compound of formula (IV), or a pharmaceutically acceptable salt thereof:

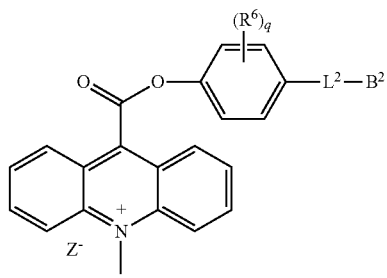
(IV)

where $L^2$ is any linker as herein described;
$B^2$ is any mitotropic agent as herein described;
each $R^6$ is independently selected from halogen (e.g. F Cl, Br, I), and $C_{1-6}$ alkyl (e.g. tBu);
q is an integer from 0 to 4, preferably 0 or 2; and
Z is a monovalent anion, e.g. a Cl, Br, I, or $CF_3SO_2$ anion.

In one embodiment of formula (IV), L represents the following group:

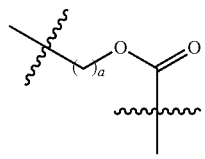

wherein a is an integer from 1 to 10, preferably 3, 4 or 5.

In one embodiment of formula (IV), $B^2$ may be the following group:

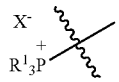

where R is as herein defined, e.g. phenyl, toluene (e.g. o-toluene, m-toluene or p-toluene), or cyclohexyl; and X is a monovalent anion, e.g. a Cl, Br, or I anion).

In certain embodiments, the chemiluminescent agent conjugate for use in the invention is a compound of formula (V), or a pharmaceutically acceptable salt thereof:

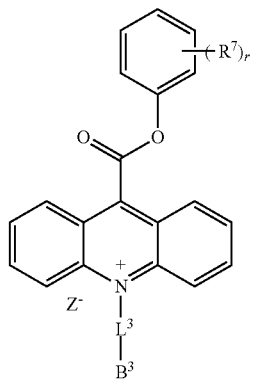
(V)

where L is any linker as herein described;
$B^3$ is any mitotropic agent as herein described;
each $R^7$ is independently selected from halogen (e.g. F, Cl, Br, I), —$CO_2R^8$ (where $R^8$ is hydrogen or $C_{1-6}$ alkyl), cyano, and $C_{1-6}$ alkyl (e.g. tBu);

r is an integer from 0 to 5, preferably 0 or 3; and

Z is a monovalent anion, e.g. a Cl, Br, I, or $CF_1SO_2$ anion.

In formula (V), L is preferably $C_{1-10}$ alkylene, e.g. $C_{1-6}$ alkylene.

In one embodiment of formula (IV), $B^3$ may be the following group:

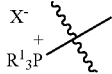

where $R^1$ is as herein defined, e.g. phenyl, toluene (e.g. o-toluene, m-toluene or p-toluene), or cyclohexyl; and X is a monovalent anion, e.g. a Cl, Br, or I anion).

In certain embodiments, the chemiluminescent agent conjugate for use in the invention is a compound of formula (VI), or a pharmaceutically acceptable salt thereof:

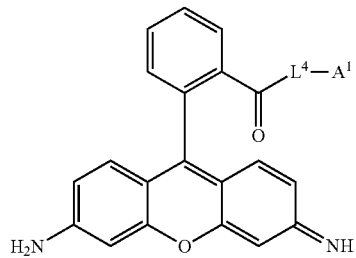

(VI)

where $L^4$ is any linker as herein described; and $A^1$ is any chemiluminescent moiety as herein described.

In formula (VI), $L^4$ may be selected from the following:

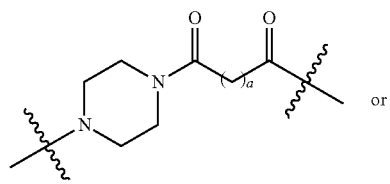

where a is an integer from 1 to 10, preferably 4, 5 or 6.

In one embodiment of formula (VI), $A^1$ is selected from any of the following:

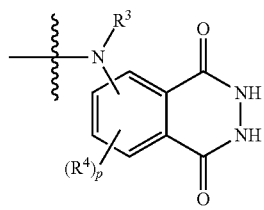

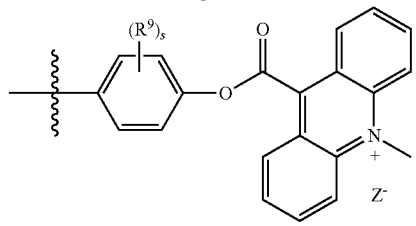

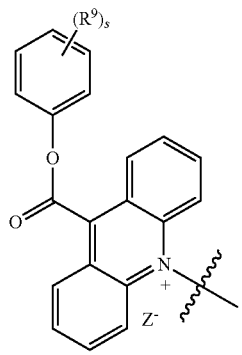

where $R^3$ is hydrogen, or an alkyl group such as C alkyl (e.g. methyl);

each $R^4$ is independently selected from $C_{1-6}$ alkyl, and $-NR^5R^6$;

$R^5$ and $R^6$ are independently selected from H and $C_{1-6}$ alkyl, preferably from H and $C_{1-3}$ alkyl (e.g. $-CH_3$);

p is an integer from 0 to 3, preferably 0, 1 or 2, e.g. 0 or 1;

Z is a monovalent anion, e.g. a Cl, Br, I, or $C_3OSO_2$ anion;

each $R^9$ is independently selected from halogen (e.g. F, Cl, Br, I) and $C_6$ alkyl (e.g. tBu); and s is an integer from 0 to 4, preferably 0, 2 or 3.

In certain embodiments, the chemiluminescent agent conjugate for use in the invention is a compound of formula (VII), or a pharmaceutically acceptable salt thereof:

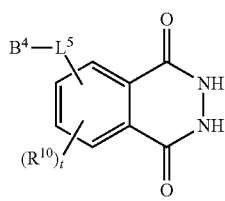

(VII)

where $L^5$ is any linker as herein described;

$B^4$ is any mitotropic agent as herein described;

each $R^{10}$ is independently selected from $C_{1-6}$ alkyl (e.g. methyl), and $-NR^{11}R^{12}$;

$R^{11}$ and $R^{12}$ are independently selected from H and $C_{1-6}$ alkyl, preferably from H and $C_{1-3}$ alkyl (e.g. $-CH_3$); and t is an integer from 0 to 3, preferably 1 or 2.

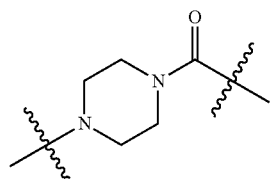

Preferred compounds of formula (VII) include the following compounds of formula (VIIa):

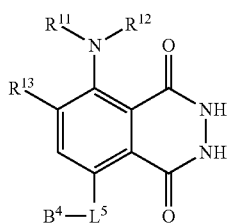

(VIIa)

where $L^5$, $B^4$, $R^{11}$ and $R^{12}$ are as herein defined; and R is H or $C_{1-3}$ alkyl.

In formulae (VII) and (VIIa), $L^5$ is preferably $C_{1-11}$ alkylene, more preferably $C_{2-8}$ alkylene, e.g. propylene.

The chemiluminescent agent conjugates herein described may be prepared using methods and procedures known in the art. Methods which may be used for covalently attaching a chemiluminescent agent to the mitotropic moiety include known coupling techniques. The exact method used will be dependent on the exact nature of the chemiluminescent agent, the mitotropic agent and the linker (where present), specifically the nature of any pendant functional groups involved in forming the linkage. Where pendant functional groups are already present on the binding partners these may be employed in linking the various moieties. If necessary, one or more components of the conjugate (i.e. the chemiluminescent moiety, the linker, and the mitotropic moiety) may be functionalised, e.g. to include reactive functional groups which may be used to couple the components. Suitable reactive groups include carboxylic acid, hydroxy, thiol, carbonyl, acid halide, primary and secondary amines, aryl halides and pseudohalides, alkyl halides and pseudohalides, alkenyl halides and pseudohalides, terminal alkynes, clickable moieties, etc. Methods for the introduction of such functional groups are well known in the art.

Examples of methods which may be used to covalently link the chemiluminescent agent to one or more mitotropic agents include, but are not limited to, the following: amide bond formation, ether bond formation, ester bond formation, thioester bond formation, cross-coupling reactions, olefin metathesis reactions, electrophilic aromatic substitutions, click chemistry, nucleophilic substitution reactions, etc.

Compounds for use as starting materials in the preparation of the conjugates herein described are either known from the literature or may be commercially available. Alternatively, these may readily be obtained by methods known from the literature. A more detailed description of how to prepare the compounds for use in accordance with the invention is found in the Examples.

The chemiluminescent agent conjugates as herein described are in themselves novel and form a further aspect of the invention. Methods for their preparation comprising the step of linking one or more chemiluminescent agents to one or more mitotropic agents, for example using any of the techniques herein described, form a further aspect of the invention.

For use in PDT, the mitotropic chemiluminescent agents herein described are used in combination with a photosensitizer or a precursor of a photosensitizer. Key to the invention is that these should come into close proximity to one another in the cell mitochondria in order that the chemiluminescent agent can 'activate' the photosensitizing agent. These agents may be provided individually for separate, simultaneous or sequential administration to the patient in a method of PDT. Alternatively, these may be provided in a single formulation in which both the mitotropic chemiluminescent agent and the photosensitizer (or precursor) are present. Such formulations form part of the invention.

For use in the invention, any photosensitizer (or photosensitizer precursor) should be capable of accumulating in the mitochondria of the target cells following its in vivo administration to ensure that this comes into close proximity to the chemiluminescent compound. For example, this may be a mitochondria-localising photosensitizer or precursor thereof.

Examples of photosensitizing agents and precursors which are capable of targeting the mitochondria include: 5-ALA and its derivatives, mTHPC, temoporfin, chlorin e6, sulphonated aluminium phthalocyanines, anthraquinones and derivatives thereof (e.g. hypericin, hypocrellins [A, B], cercosporin, calphostin, elsinochromes [A, B, C]), and their pharmaceutically acceptable salts. Other mitochondria-accumulating photosensitizing agents are known in the art and these may also be used in the invention.

Other known photosensitizers and precursors may be used in the invention subject to appropriate modification to confer the desired targeting properties. For example, these may be encapsulated within a suitable nanocarrier which has mitochondrial-targeting ability. In these embodiments, a wider range of photosensitizers may be used and it is envisaged that any known photosensitizer (or precursor) suitable for use in PDT may be employed. A range of suitable agents are known in the art and include, for example, 5-aminolevulinic acid (5-ALA) and derivatives of 5-ALA (leading to production of protoporphyrin IX); mitotropic porphyrins; phthalocyanines such as aluminium phthalocyanines which may be sulphonated (i.e. AlPcS), e.g. di-sulphonated aluminium phthalocyanines such as $AlPcS_2$ or $APcS_{2a}$, or aluminium phthalocyanine tetra-sulfonate ($AlPcS_4$); sulphonated tetra-phenylporphyrins (e.g. $TPPS_{2a}$, $TPPS_4$, $TPPS_1$ and $TPPS_2$); chlorins such as tetra(m-hydroxyphenyl)chlorins (n-THPC) (e.g. temoporfin which is marketed under the tradename Foscan); chlorin derivatives including bacteriochlorins and ketochlorins; mono-L-aspartyl chlorin e6 (NPe6) or chlorin e6; natural and synthetic porpyhrins including hematoporphyrin and benzoporphyrins; anthraquinones and derivatives thereof (e.g. hypericin, hypocrellins [A, B], cercosporin, calphostin, elsinochromes [A, B, C]).

Pharmaceutically acceptable salts of any of these photosensitizers (or precursors) may also be used. Such salts include salts with pharmaceutically acceptable organic or inorganic acids or bases.

Derivatives of 5-ALA which may be used in the invention include any derivative of 5-ALA capable of forming PpIX in vivo. Typically, such derivatives will be precursors of PpIX in the biosynthetic pathway for heme and which are therefore capable of producing PpIX at the target site following administration. Suitable precursors of PpIX include 5-ALA prodrugs such as 5-ALA esters.

The following are amongst the preferred photosensitizers and precursors for use in the invention: 5-ALA, mTHPC, temoporfin, chlorin e6, sulphonated aluminium phthalocyanines, anthraquinones and derivatives thereof (e.g. hypericin, hypocrellins [A, B], cercosporin, calphostin, elsinochromes [A, B, C]), and their pharmaceutically acceptable salts. Particularly preferred for use in the invention is 5-ALA and its pharmaceutically acceptable derivatives (e.g. pharmaceutically acceptable salts, or methyl or hexyl esters).

The particular choice of chemiluminescent moiety will be dependent on various factors, including the nature of the tumour to be treated, but can readily be selected by those skilled in the art. As will be understood, the choice of chemiluminescent agent will also be dependent on the photosensitizer to be used in the PDT treatment since the wavelength of light it emits should be suitable for photoactivation of the photosensitizer.

Examples of suitable chemiluminescent agent—photosensitizer "pairs" may readily be determined by those skilled in the art. The following are provided by way suitable non-limiting examples. Where the photosensitizer is PpIX (e.g. produced in vivo following administration of 5-ALA), luminol or isoluminol may be used as the chemiluminescent agent. The photosensitizer hypericin is particularly suitable for use with the chemiluminescent agent lucigenin since these moieties can form pi-stacks for very efficient intramolecular energy transfer especially in the presence of binding agents such as the metal chelators DTPA or EDTA. Luminol and mTHPC represent a very efficient energy transfer pair. Other efficient energy transfer pairs include luminol-erythrosine B, luminol-hypocrellins, luminol-cercosporin, luminol-calphostin, luminol-elsinochromes acridine esters-hypocrellins, lucigenin-hypocrellins, acridine esters-cercosporin, lucigenin-cercosporin, acridine esters-hypericin, and lucigenin-hypericin. Haematoporphyrin derivative (HPD) or sulphonated aluminium phthalocyanine may be used with either luminol or lucigenin. However, these are only indicative examples of potential functional pairs and others can readily be determined by those skilled in the art.

The mitotropic chemiluminescent agents herein described are intended for use in methods of photodynamic therapy and are suitable for use in the treatment of disorders or abnormalities of cells or tissues within the body which are responsive to photodynamic therapy. Such methods will involve the simultaneous, separate or sequential use of a photosensitizer or a precursor of a photosensitizer as herein described.

In general, cells which are metabolically active are responsive to photodynamic treatment. Examples of metabolically active cells are those which undergo abnormal growth, such as an increased number of cells/increased cell proliferation, abnormal maturation and differentiation of cells, or abnormal proliferation of cells. Any condition characterised by such a growth pattern may be treated in accordance with the PDT methods herein described.

Disorders or abnormalities which may be treated include malignant and pre-malignant cancer conditions, such as cancerous growths or tumours, and their metastases; tumours such as sarcomas and carcinomas, in particular solid tumours. The invention is particularly suitable for the treatment of tumours, especially those which are located below the surface of the skin, i.e. internal cancers or deeply-sited cancers.

PDT in accordance with the invention may be applied in two ways: (i) as a treatment for malignant or pre-malignant conditions (e.g. gliomas) without the need for an external light source as in classical PDT; or (ii) as a repeatable, adjuvant, post-operative, photochemical treatment to subdue any active neoplastic foci left behind, which could lead to either recurrence or disease dissemination. The treatment may be effectively used to manage and contain the condition (e.g. brain cancer) for life through repeated treatment sessions. Treatment of occult metastasis of the primary disease may also be carried out without the need for previous diagnosis.

Examples of tumours that may be treated using the invention are sarcomas, including osteogenic and soft tissue sarcomas; carcinomas, e.g. breast, lung, cerebral, bladder, thyroid, prostate, colon, rectum, pancreas, stomach, liver, uterine, hepatic, renal, prostate, cervical and ovarian carcinomas; lymphomas, including Hodgkin and non-Hodgkin lymphomas; neuroblastoma, melanoma, myeloma, Wilm's tumour; leukemias, including acute lymphoblastic leukaemia and acute myeloblastic leukaemia; astrocytomas, gliomas and retinoblastomas; mesothelioma. However, the invention finds particular value in the treatment of deep lying cancerous lesions that are difficult to access non-invasively. Treatment of gliomas (e.g. GMB) forms a preferred aspect of the invention.

Other examples of metabolically active cells are inflamed cells. Inflammatory diseases such as rheumatoid arthritis may thus also be treated using the PDT methods in accordance with the invention.

For use in any of the PDT methods herein described, the mitochondria-targeted chemiluminescent agent will generally be provided in a pharmaceutical composition with at least one pharmaceutically acceptable carrier or excipient. Such compositions form a further aspect of the invention. These may also comprise the selected photosensitizer (or precursor), although it is envisaged that in most cases the photosensitizer (or its precursor) will be provided in a different formulation for separate administration to the patient.

The pharmaceutical compositions as herein described may be formulated using techniques well known in the art. The route of administration will depend on the intended use and, in particular, the location of the cells or tissues to be treated. Typically, these will be administered systemically and may thus be provided in a form adapted for parenteral administration, e.g. by intradermal, subcutaneous, intraperitoneal, intravenous or intratumoural injection, or by infusion via a drip. Suitable pharmaceutical forms include suspensions and solutions which contain the conjugate and/or the photosensitizer (or its precursor) together with one or more inert carriers or excipients. Suitable carriers include saline, sterile water, phosphate buffered saline and mixtures thereof. Preferably, the compositions will be used in the form of an aqueous suspension or solution in water or saline, e.g. phosphate-buffered saline.

The compositions may additionally include other agents such as emulsifiers, suspending agents, dispersing agents, viscosity modifiers, solubilising agents, stabilisers, buffering agents, preserving agents, etc. The compositions may be sterilised by conventional sterilisation techniques.

In one embodiment the mitochondria-targeted chemiluminescent agent is provided in the form of a solution in water or in saline (or in any other pharmaceutically relevant, biocompatible vehicle) which is suitable for injection intravenously or intratumourally. This may be administered either as a single dose or in repeated doses.

In one embodiment the chemiluminescent agent conjugate may be administered in the form of a slow release formulation. Suitable delayed release formulations are known in the art and include any formulation which is capable of the continuous slow release of the agent in vivo.

One example of a suitable delayed release formulation is an injectable implant which provides for sustained release in vivo. Such an implant may be an in situ forming implant based on biocompatible and biodegradable polymers containing nanoparticles of the active compounds. These will provide sustained delivery of the chemiluminescent agent to assure prolonged luminescence, thereby achieving optimised therapeutic effect of the treatment.

In another aspect, the chemiluminescent conjugate may be provided in the form of thermoresponsive formulations which become thermogels at physiological temperature (i.e. once delivered to the body). These can be formulated to optimally release their load over a period of up to 15 hours, e.g. 10 to 15 hours. The use of temperature-responsive polymers allows the formulation of low viscosity solutions which are suitable for subcutaneous injection and which, in response to body temperature, undergo an in situ phase-transition and turn into a gel. To optimise the thermosetting properties of the gel-network different polymers and their copolymers may be used. Such polymer materials are known and used in the art and include, for example: poly(lactic-co-glycolic acid) (PLGA); alginate/hyaluronic acid; poly(N-isopropylacrylamide); and poloxamers.

Nanoparticles and/or microparticles containing the chemiluminescent conjugates may also be provided in order to provide a controlled and continuous release of the active over a prolonged period, e.g. over 10 to 15 hours. Examples of such carriers include (i) micellar carriers, (ii) liposomes, (iii) dendrimeric or polymeric nanocarriers, and (iv) solid lipid nanoparticles. Any such particles may be included in the thermoresponsive formulations herein described such that these form a reservoir for release of the active in the in situ produced gel network.

The compositions herein described may be administered systemically (e.g. orally or parenterally), or alternatively these may be locally applied (e.g. topically) at or near the affected site. The route of administration will depend on the severity, nature and location of the disease to be treated as well as the photosensitizer (or precursor) used. Compositions that may be administered systemically include plain or coated tablets, capsules, suspensions and solutions. Compositions that may be administered locally (e.g. topically) include gels, creams, ointments, sprays, lotions, and any of the other conventional pharmaceutical forms in the art. Creams, ointments and gels may be formulated with an aqueous or oily base with the addition of suitable thickening and/or gelling agents.

Typically, the methods herein described might involve the initial step of administration of an effective amount of a composition which contains the photosensitizer, e.g. by intravenous injection. The photosensitizer (or precursor) is then allowed to distribute to the desired target area of the body and to allow for in situ generation of the active photosensitizing agent, e.g. PpIX, prior to administration of the mitochondrial-targeted chemiluminescent agent, e.g. intravenously either by injection and/or a drip. The time profile for PpIX generation in cells following 5-ALA administration can be several hours (typically this might peak between 2-10 hours after administration), hence it is desirable to delay the delivery of the mitochondrial-targeted chemiluminescent agent. This can either be achieved by delaying its administration or by means of delayed release formulations as herein described. Whilst it is envisaged that administration of the photosensitizer will typically take place prior to administration of the mitochondrial-targeted chemiluminescent agent, delivery of these may nevertheless be simultaneous, for example, where the mitochondrial-targeted chemiluminescent agent is provided in the form of a delayed release formulation (e.g. in the form of any of the nanoparticulate and/or microparticulate carrier systems as herein described).

For example, the patient may first have a 5-ALA injection and then at the right timeframe and within the appropriate therapeutic window, will receive either a second injection of the mitochondrial-targeted chemiluminescent agent (e.g. 'mitotropic' luminol) or will be placed on a drip containing this agent for as long as required. This set-up is minimal in demands subject to any post-treatment monitoring.

The effective dose of the compositions herein described, the number of doses, and precise timing for administration will depend on various factors, including the nature of the mitochondrial-targeted chemiluminescent agent, the photosensitizer (or precursor), their mode(s) of administration, the condition to be treated, the patient, etc., and may be adjusted accordingly.

A further aspect of the invention relates to a method of photodynamic therapy of cells or tissues of a patient, said method comprising the step of administering to said cells or tissues:
  (a) an effective amount of a mitochondrial-targeted chemiluminescent agent as herein described and, simultaneously, separately, or sequentially thereto, an effective amount of a photosensitizer or photosensitizer precursor; or
  (b) an effective amount of a pharmaceutical composition which comprises a mitochondrial-targeted chemiluminescent agent as herein described and a photosensitizer or photosensitizer precursor.

In a further aspect the invention provides a product comprising a mitochondrial-targeted chemiluminescent agent as herein described, and a photosensitizer or precursor for simultaneous, separate or sequential use in a method of photodynamic therapy, e.g. in any of the PDT methods herein described.

In a still further aspect the invention provides a kit comprising: (i) a mitochondrial-targeted chemiluminescent agent as herein described; and separately (ii) a photosensitizer or photosensitizer precursor; and optionally (iii) instructions for the use of (i) and (ii) in a method of photodynamic therapy. When used, the active components of the kit (i.e. (i) and (ii)) may be administered simultaneously, separately or sequentially.

The invention will now be described further with reference to the following non-limiting Examples and the accompanying drawings in which:

FIG. 1—A schematic representation of the concept behind the invention in which a modified version of luminol is employed as a self-sustained, intracellular source of light and the target mitochondria is used as the power supply for "switching on the light" and activating the cytotoxic activity of the photosensitive drug (PpIX) from within the tumour cells. This representation is not to be construed as limiting in any way on the scope of the invention.

Figure 2:
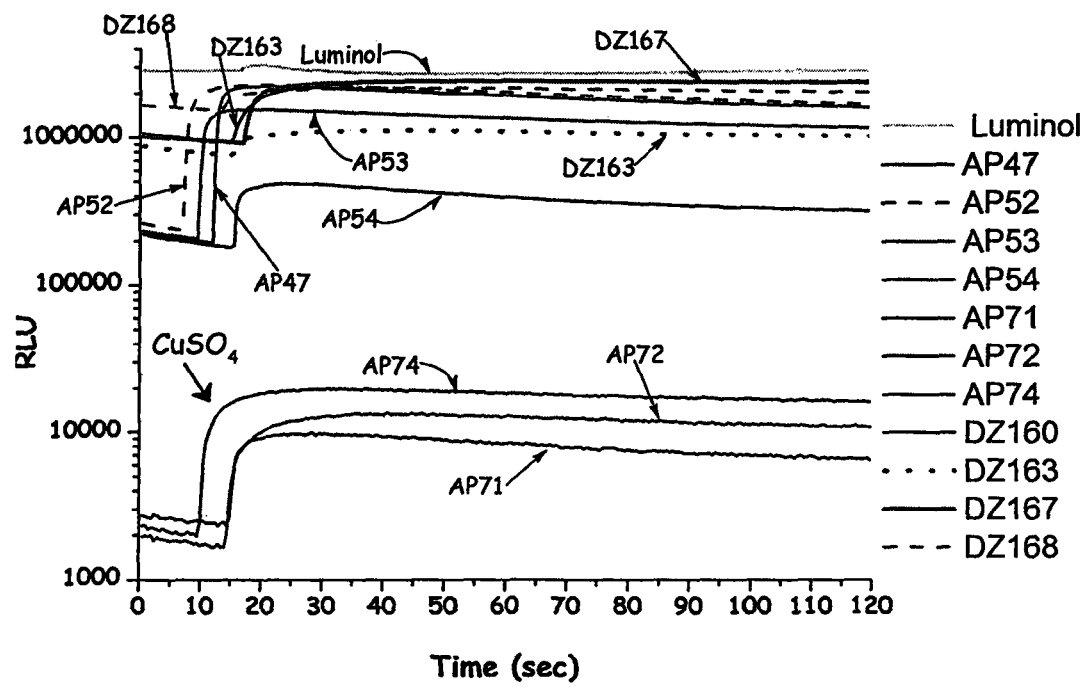

FIG. 2—Luminescence of mitotropic luminol derivatives in biomimetic conditions resembling the mitochondrial matrix environment.

Figure 3:
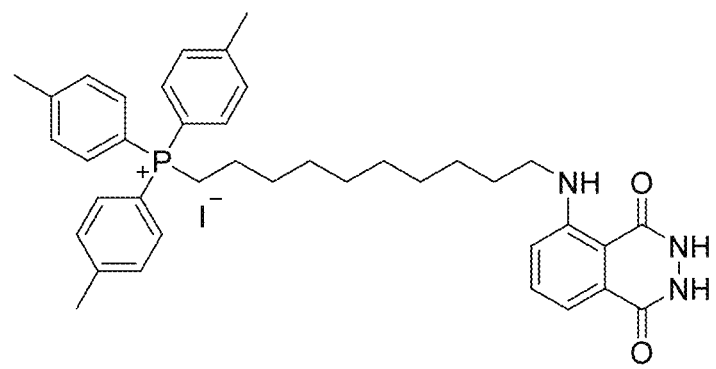
Figure 3:
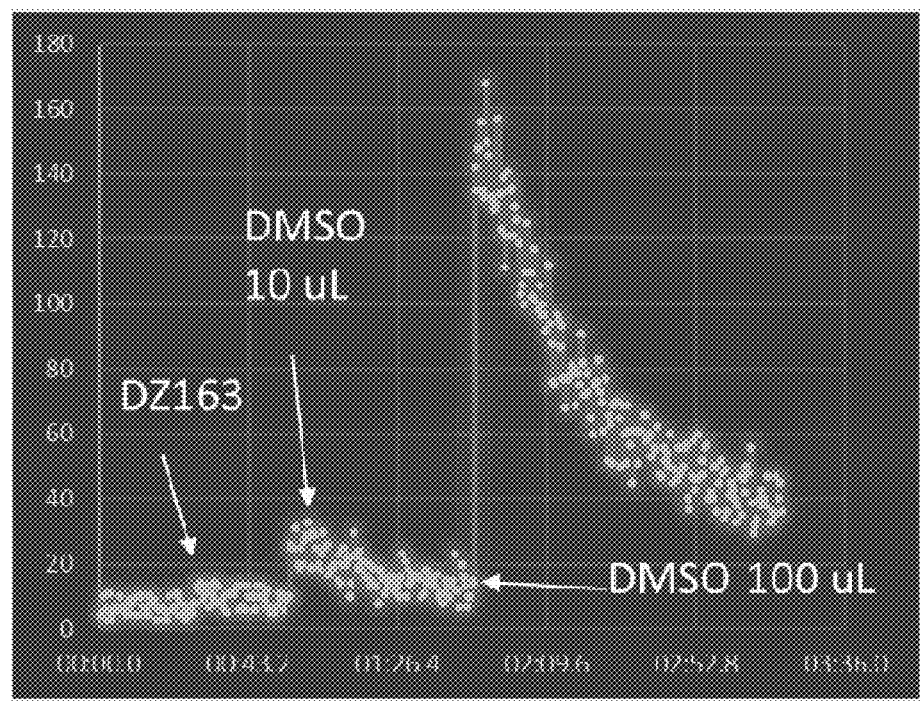

FIG. 3—Luminescence from a cell layer after application of mitotropic luminol derivatives in propylene glycol.

Figure 4:
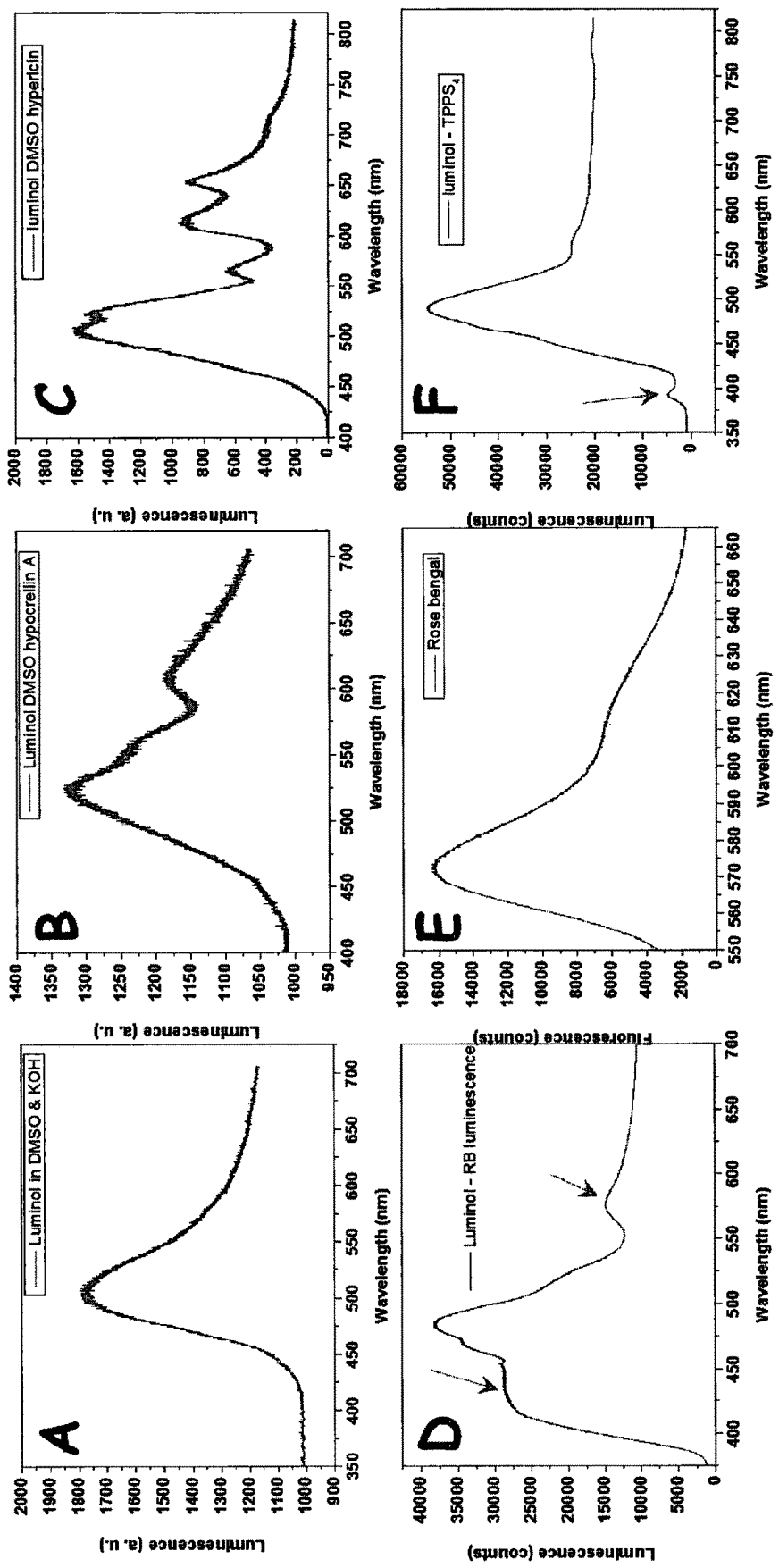

FIG. 4—Energy transfer between luminol luminescence and various photosensitisers: A) luminescence of luminol in alkaline DMSO (KOH); B) addition of hypocrellin A (HYPA); C) addition of hypericin (HYP) instead of HYPA; D) Luminol in aqueous carbonate buffer (pH 10.3) with the addition of $CuSO_4$ and urea peroxide in the presence of Rose Bengal (RB); E) 532 nm laser excitation; F) the luminol system in carbonate buffer as in D) but with the addition of TPPS4.

Figure 5:
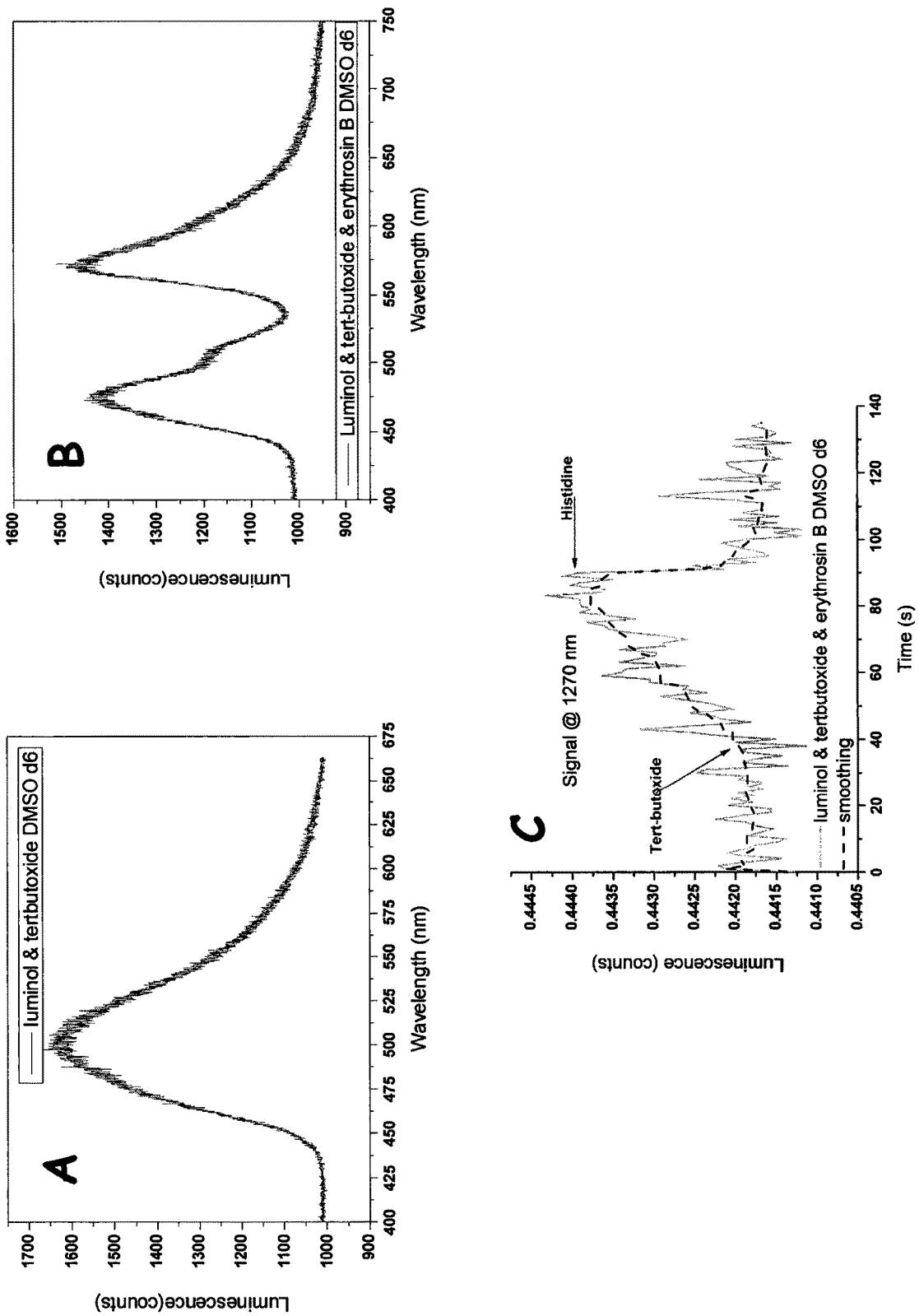

FIG. 5—Energy transfer between luminol luminescence and various photosensitisers: A) the spectrum of luminol in DMSO-tert-butoxide; B) Erythrosin B absorbs very strongly, especially around 500 and demonstrates very strong fluorescence around 580 nm; C) addition of tert butoxide to the DMSO-luminol solution.

Figure 6:
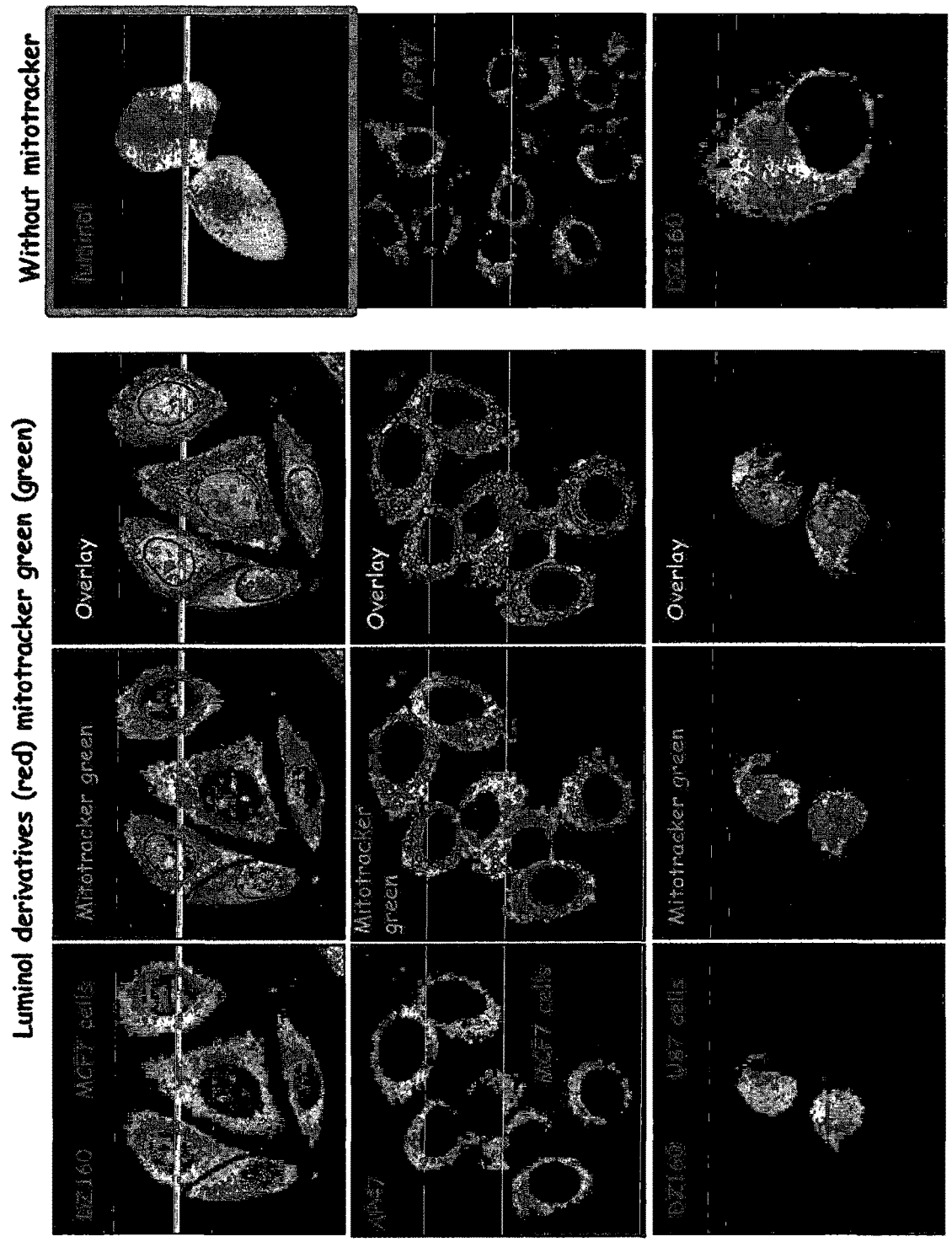

FIG. 6—Confocal micrographs of mitotropic luminol derivatives and luminol. On the triple column (left) the mitochondrial localisation of two derivatives namely DZ160 and AP47 is shown in two different cell lines, the breast adenocarcinoma cell line MCF7 and the glioblastoma cell line U87. The three micrographs in each row of this triple column depict the localisation of the derivative, the localisation of the mitochondrial marker mitotracker green and the overlay of these two localisations in a merged image. The fluorescence of luminol is represented in the left column while mitotracker green fluorescence is shown in the middle column. Their overlay is shown in the third column. On the column in the right (fourth column) the cytosolic localisation of free luminol is shown on the top (with border) while in two cases the localisation of AP47 and DZ160 is depicted in cells not incubated with mitotracker green to exclude fluorescence spillover and hence cross talk between the mitotracker and luminol-derivative channels.

Figure 7:
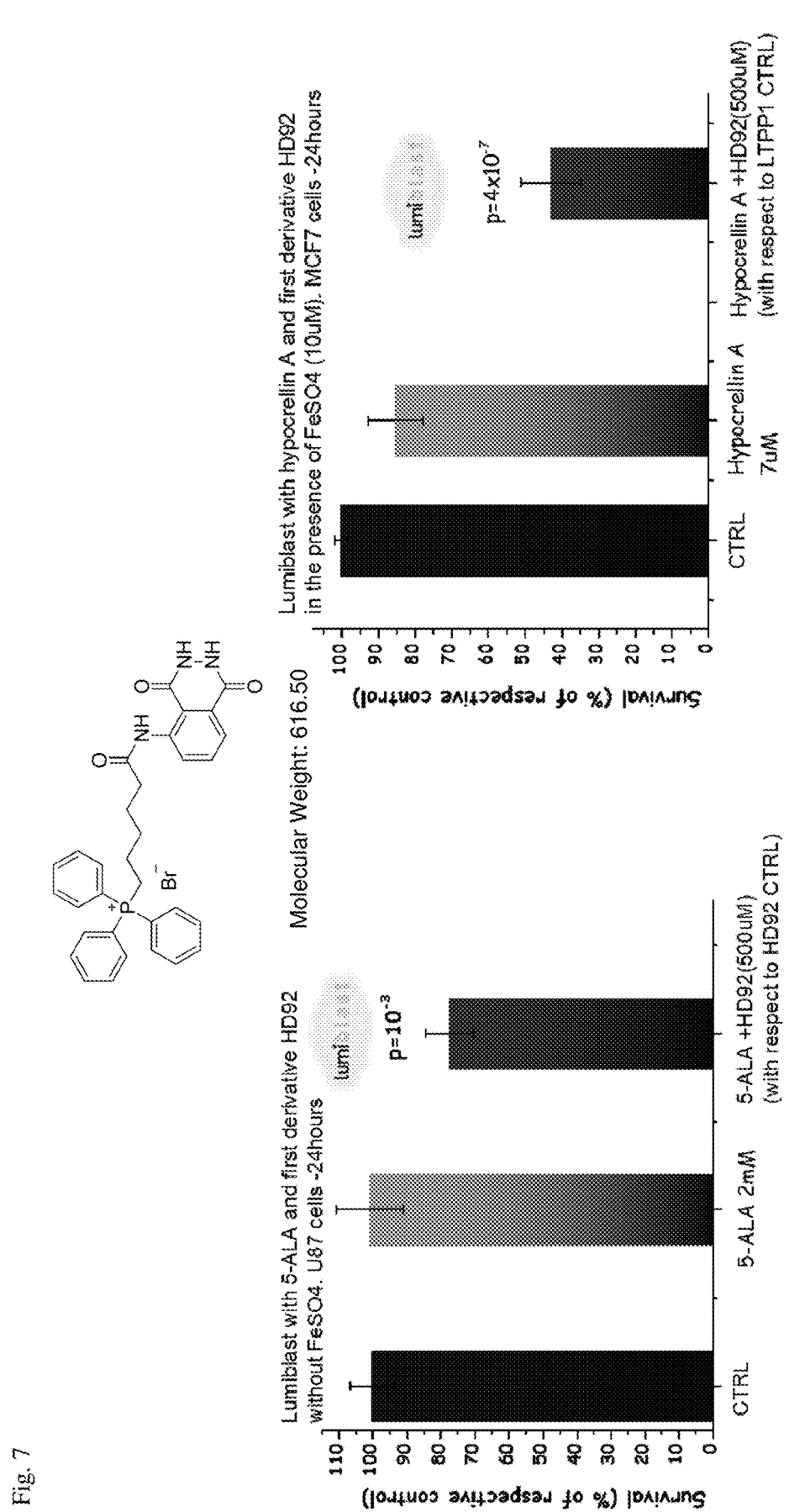

FIG. 7—LUMIBLAST experiments on U87 and MCF7 cells.

Figure 8:
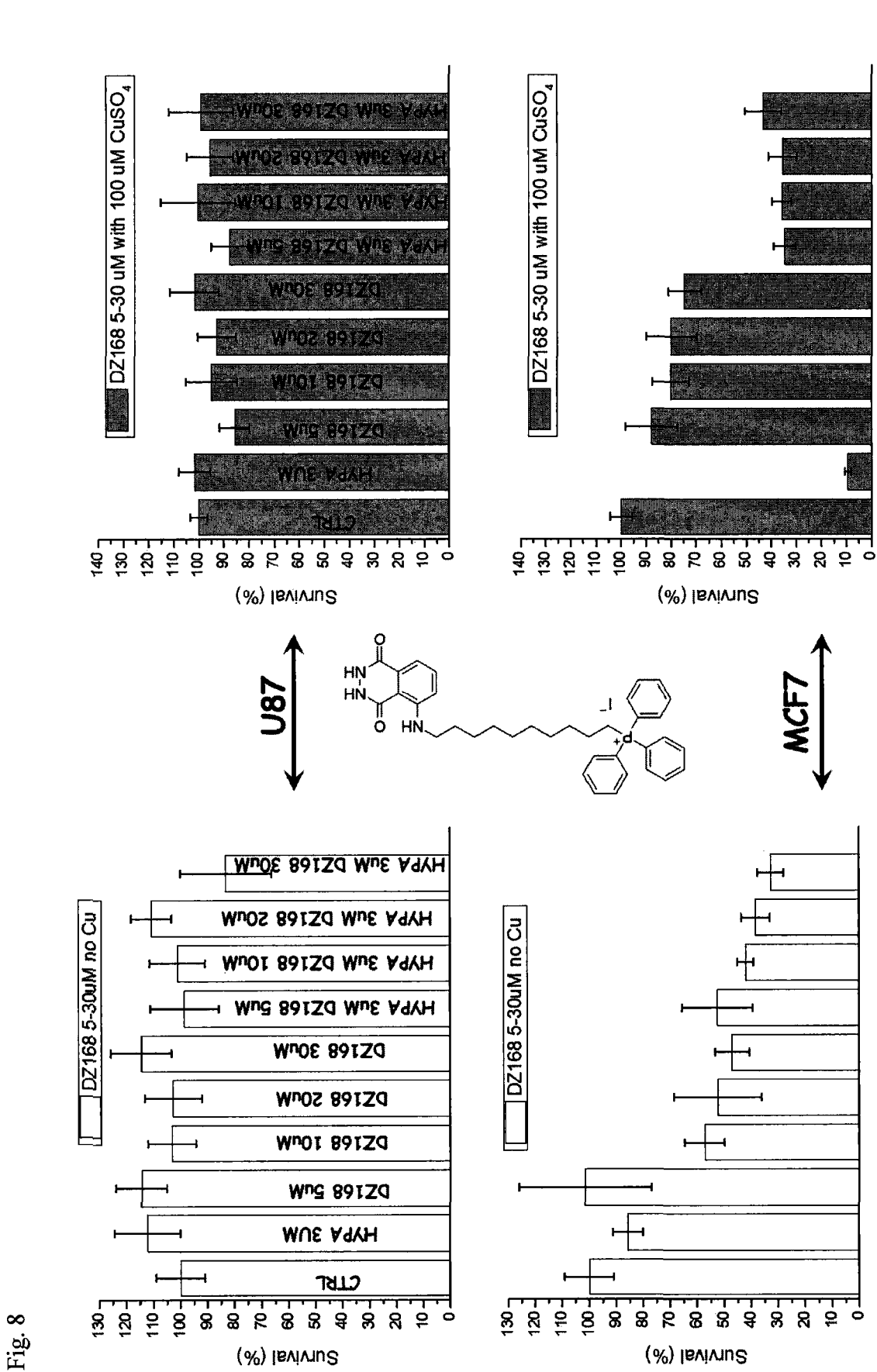

FIG. 8—Compound DZ68 in MCF7 and U87 cells in the presence of $CuSO_4$ and with the use of HYPA as the photosensitizer.

Figure 9:
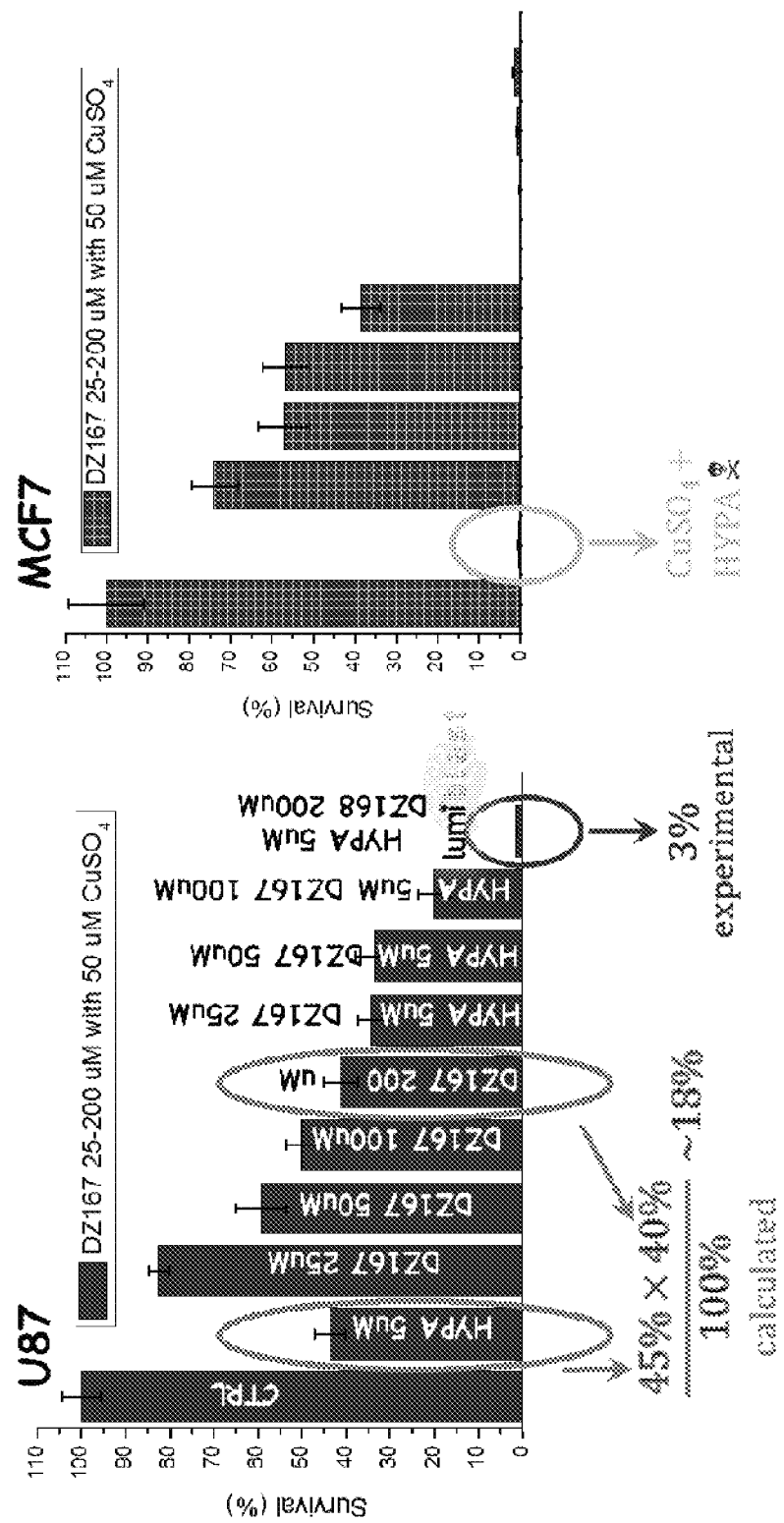

FIG. 9—LUMIBLAST effect in U87 cells mediated by $CuSO_4$ in the presence of HYPA as the photosensitizer and DZ167 triphenylphosphonium-luminol derivative.

Figure 10:
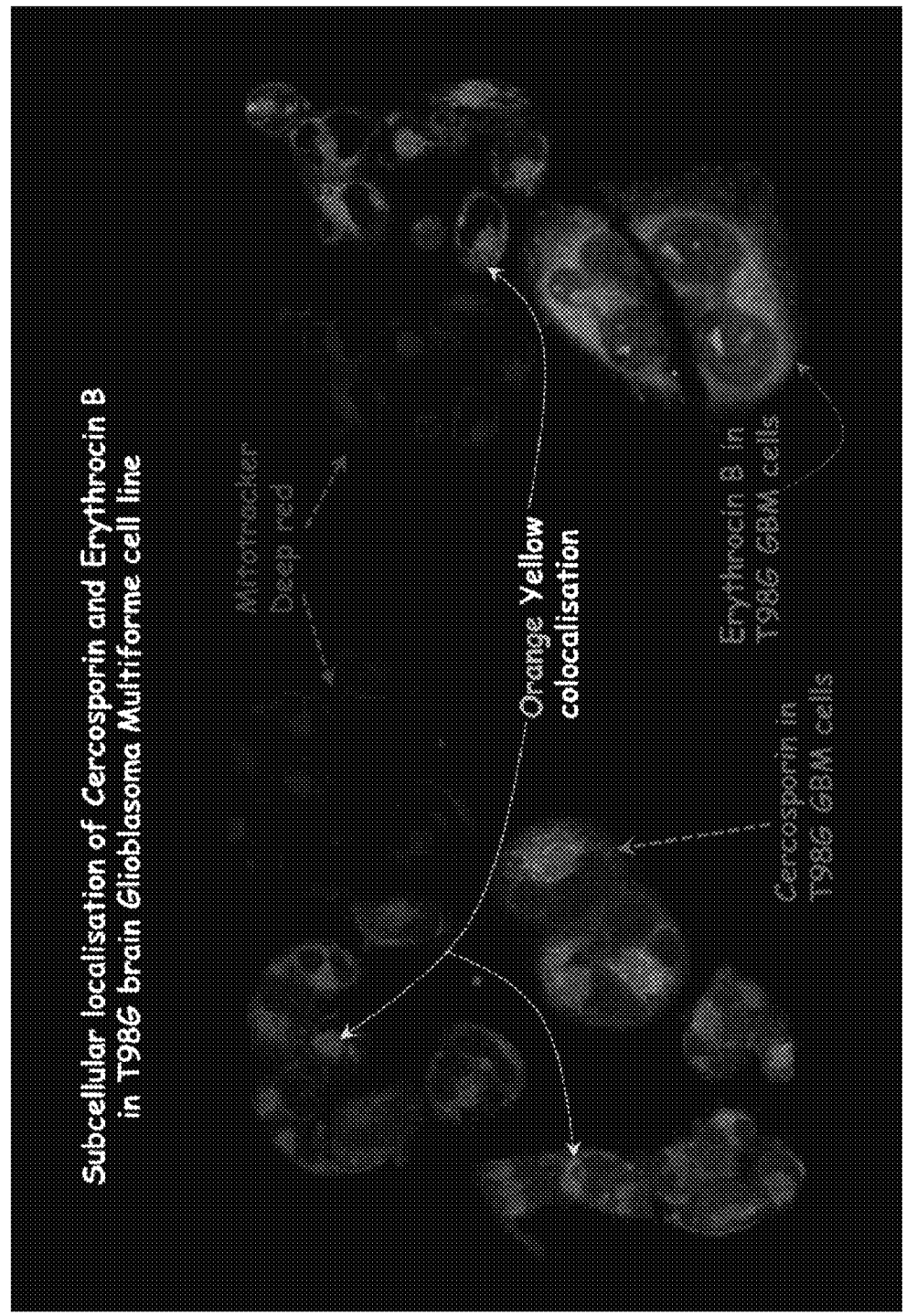

FIG. 10—Subcellular localisation of cercosporin and erythrocin b (green in image) in T98G glioblastoma multiforme cells. The probe mitotracker deep red (red in image) was used to evaluate the colocalization of the two dyes with cell mitochondria.

Figure 11:
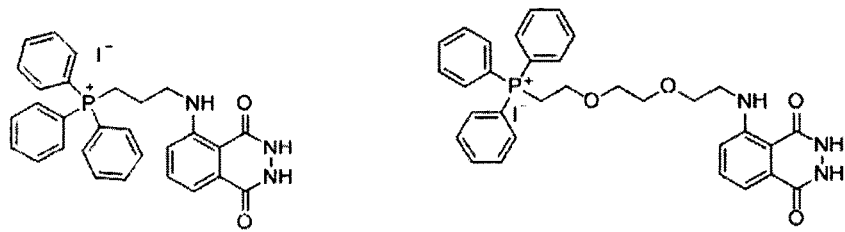
Figure 11:
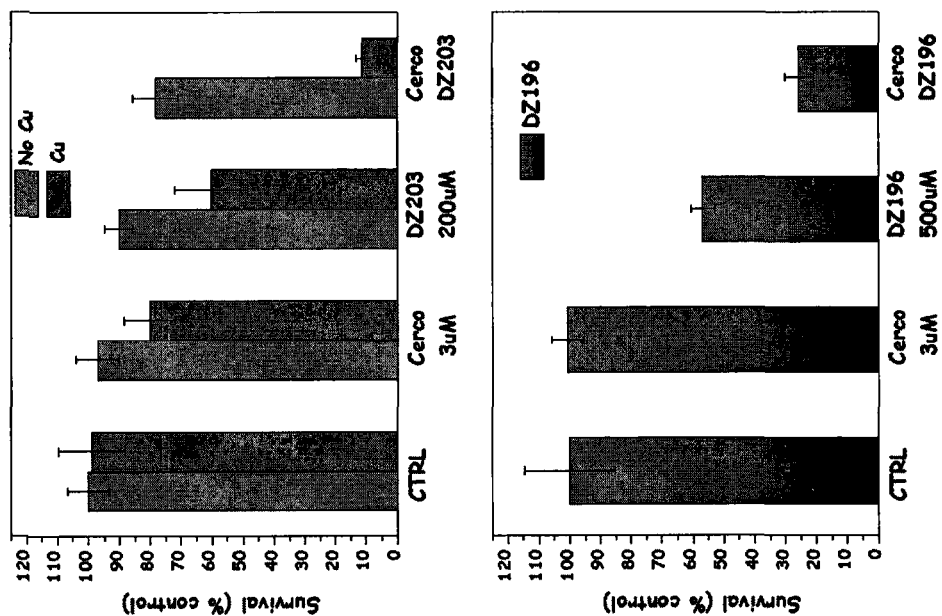
Figure 11:
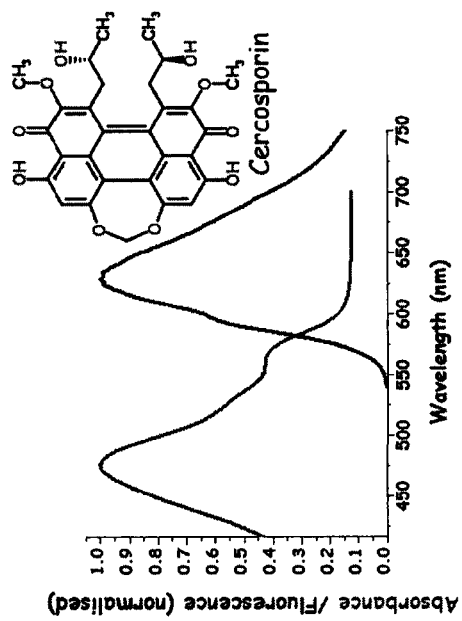
Figure 11:
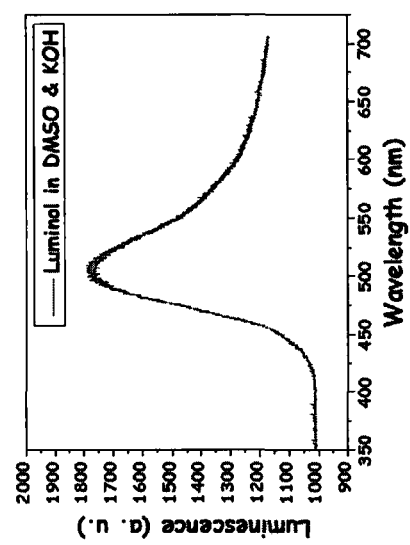

FIG. 11—LUIMIBLAST effect with the use of the photosensitizer cercosporin and two luminol mitotropic derivatives namely DZ203 and DZ196, in U87G, BM cells. The absorption and emission properties of cercosporin are shown in the left top diagram whereas the emission of luminol is shown in the left lower graph.

Figure 12:
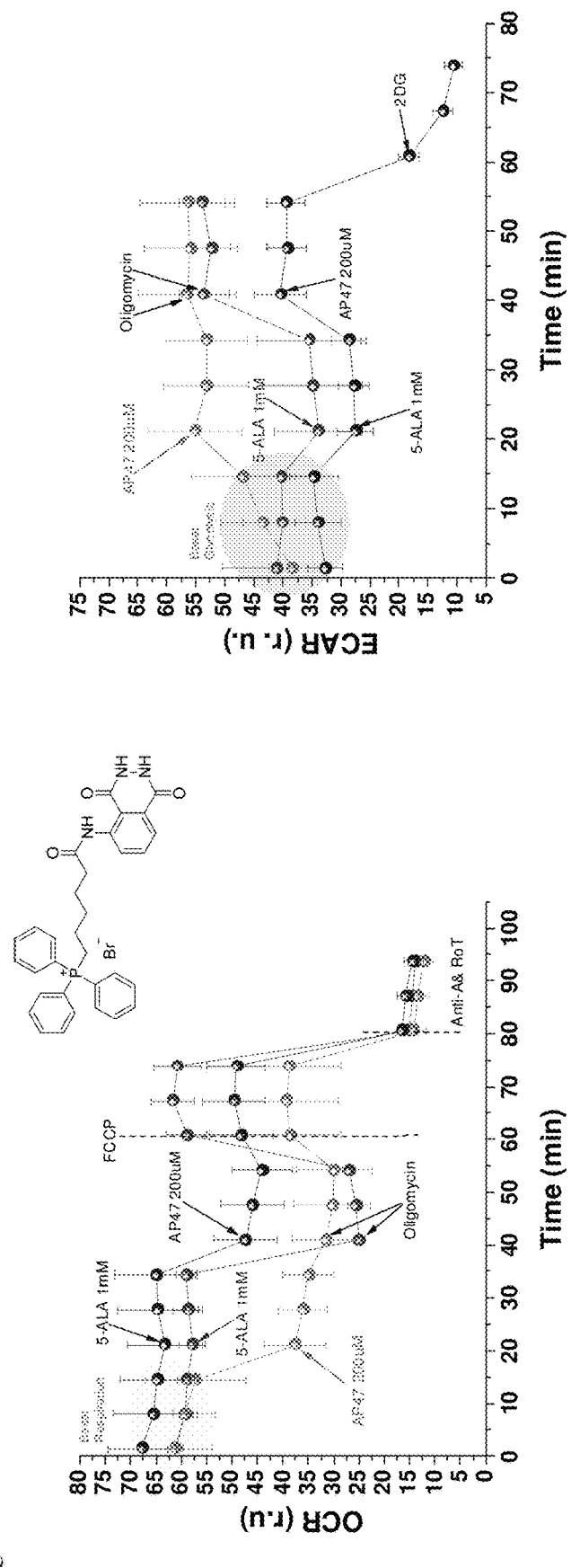

FIG. 12—Metabolic analysis on MCF7 cells incubated with DZ167 and 5-ALA individually as well as in combination (first 5-ALA and then DZ167). Oxygen consumption rate (left) represents the effects of the compounds investigated on cellular respiration while the extracellular acidification rate (ECAR) shows the effect of the selected compounds on the process of glycolysis. Following compound injections, the cells were subsequently injected with oligomycin, FCCP and Antimycin A+Rotenone in the case of single compound administration (DZ167 or 5-ALA) and FCCP and Antimycin A+Rotenone in the case of combinatory administration (5-ALA and DZ167). These subsequent injections were performed in order to elucidate the effects on cellular respiration, and in the case of oligomycin also the glycolytic capacity of the cells.

Figure 13:
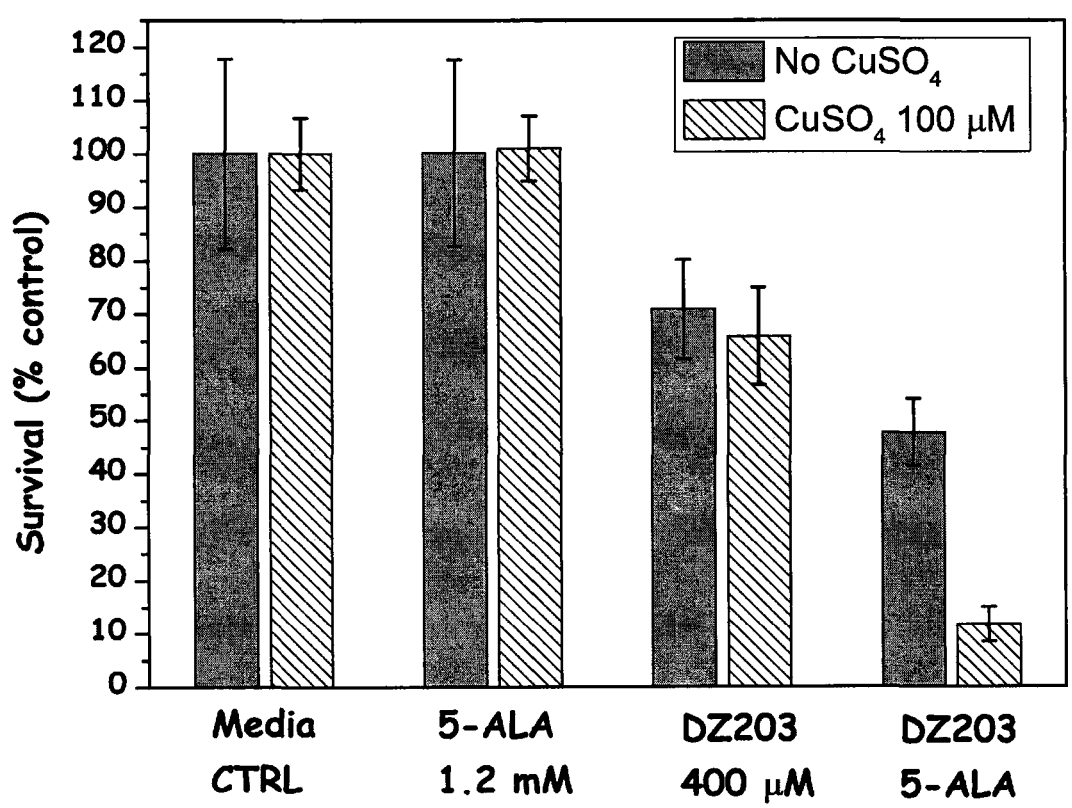

FIG. 13—LUMIBLAST effect in MDA-MB-231 breast carcinoma cells in the absence (grey bars) or presence (white bars diagonal line pattern) of 100 μM $CuSO_4$ and the co-administration of 5-ALA (1.2 mM) and DZ203 (400 μM).

EXAMPLES

Example 1—Synthesis of Phthalimides as Acylation Precursors (Intermediates)

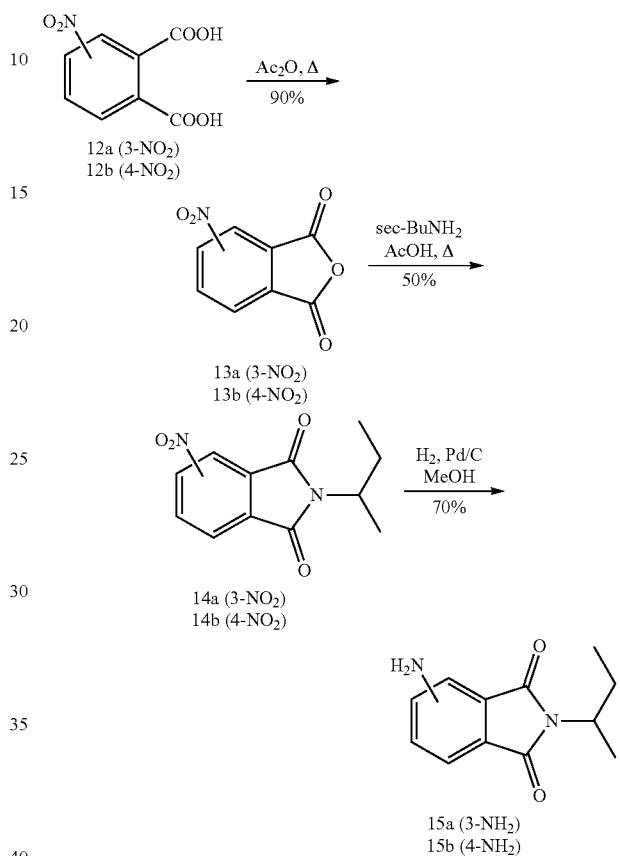

Step 1: A mixture of nitrophthalic acid 12a or 12b (12.6 g, 0.06 mol) and acetic anhydride (11.15 mL, 0.12 mol) was refluxed for 1 hour. The mixture was brought to room temperature, toluene (300 mL) was added and the volatiles were removed in vacuo. The residue was washed several times with diethyl ether to afford the respective anhydride 13a or 13b (10.25 g, 90%) as a white solid.

Step 2: To a solution of nitrophthalic anhydride 13a or 13b (10 g, 0.052 mol) in acetic acid (90 mL) was added sec-butylamine (7.85 mL, 0.078 mol) and the mixture was refluxed for 5 hours. After cooling, the mixture was concentrated in vacuo, diluted with $H_2O$ (100 mL) and extracted with DCM (3×100 mL). The combined organic layer was washed with saturated aq. $NaHCO_3$ and brine, dried over anhydrous $Na_2SO_4$, filtered and concentrated in vacuo to give the respective phthalimide 14a or 14b (6.45 g, 50%) as a white solid.

Step 3: 10% Pd/C (10 mol %) was added to a degassed (Ar purged) solution of nitrophthalimide 14a or 14b (9 g, 0.04 mol) in MeOH (250 mL) and the mixture was stirred in a hydrogen atmosphere (20 bar) for 24 hours. Then, the solution was filtered through a celite pad and the solvent was distilled off, yielding the respective phthalimide 15a or 15b (6.1 g, 70%) as a yellow solid.

Example 2—Synthesis of 6-bromo-N-(2-(sec-butyl)-1,3-dioxoisoindolin-4-yl)hexanamide (Intermediate)

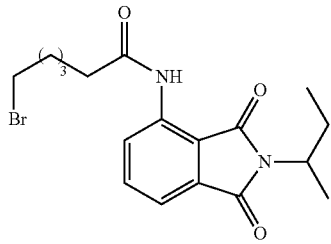

11a 6-bromohexanoic acid (2.14 g, 0.011 mol) was suspended in oxalyl chloride (ca. 10 mL), stirred at ambient temperature for 2 hours and the excess oxalyl chloride was distilled off under reduced pressure. The residue (acid chloride) was dissolved in dry dichloromethane (10 mL) and added dropwise to a solution of 15a (2.2 g, 0.01 mol) and pyridine (1.62 ml, 0.02 mol) in dry DCM (15 mL) at 0° C. under argon. After the addition, the mixture was warmed to ambient temperature and stirred for 24 hours. DCM (50 mL) was added, the solution was washed with H₂O (50 mL), 1 M aq. HCl (50 mL), saturated aq. NaHCO₃ (50 mL), and brine (50 mL), dried (Na₂SO₄) and the solvent evaporated under reduced pressure. Purification of the residue by flash chromatography (silica gel, PE/EtOAc 6:1) yielded the amide 11a (2.80 g, 71%) as a white solid.

Example 3—Synthesis of 11-bromo-N-(2-(sec-butyl)-1,3-dioxoisoindolin-4-yl)undecanamide (Intermediate)

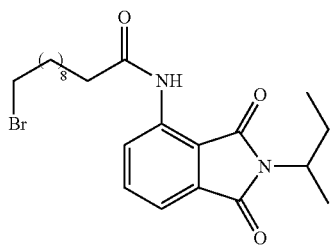

11b 11-bromoundecanoic acid (1.17 g, 4.4 mmol) was suspended in oxalyl chloride (ca. 7 mL), stirred at ambient temperature for 2 hours and the excess oxalyl chloride was distilled off under reduced pressure. The residue (acid chloride) was dissolved in dry dichloromethane (5 mL) and added dropwise to a solution of 15a (0.9 g, 4 mmol) and pyridine (0.65 ml, 8 mmol) in dry DCM (15 mL) at 0° C. under argon. After the addition, the mixture was warmed to ambient temperature and stirred for 24 hours. DCM (50 mL) was added, the solution was washed with H₂O (50 mL), 1 M aq. HCl (50 mL), saturated aq. NaHCO₃ (50 mL), and brine (50 mL), dried (Na₂SO₄) and the solvent evaporated under reduced pressure. Purification of the residue by flash chromatography (silica gel, PE/EtOAc 6:1) yielded the amide 11a (1.3 g, 70%) as a white solid.

Example 4—Synthesis of 6-bromo-N-(2-(sec-butyl)-1,3-dioxoisoindolin-5-yl)hexanamide (Intermediate)

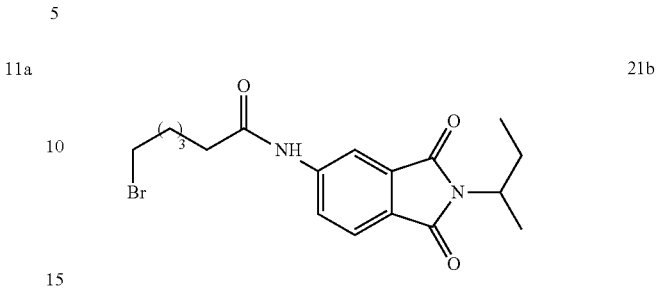

21b 6-bromohexanoic acid (1.29 g, 7 mmol) was suspended in oxalyl chloride (ca. 10 mL), stirred at ambient temperature for 2 hours and the excess oxalyl chloride was distilled off under reduced pressure. The residue (acid chloride) was dissolved in dry dichloromethane (5 mL) and added dropwise to a solution of 15b (1.3 g, 6 mmol) and pyridine (0.98 ml, 12 mmol) in dry DCM (10 mL) at 0° C. under argon. After the addition, the mixture was warmed to ambient temperature and stirred for 24 hours. DCM (50 mL) was added, the solution was washed with —H₂O (50 mL), 1 M aq. HC (50 mL), saturated aq. NaHCO₃ (50 mL), and brine (50 mL), dried (Na₂SO₄) and the solvent evaporated under reduced pressure. Purification of the residue by flash chromatography (silica gel, 4% MeOH/DCM) yielded the amide 21a (1.12 g, 47%) as a white solid.

Example 5—Synthesis of 11-bromo-N-(2-(sec-butyl)-1,3-dioxoisoindolin-5-yl)undecanamide (Intermediate)

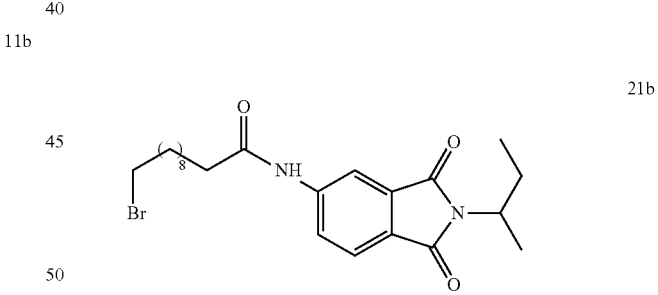

21b 11-bromoundecanoic acid (1.74 g, 7 mmol) was suspended in oxalyl chloride (ca. 7 mL), stirred at ambient temperature for 2 hours and the excess oxalyl chloride was distilled off under reduced pressure. The residue (acid chloride) was dissolved in dry dichloromethane mL) and added dropwise to a solution of 15b (1.3 g, 6 mmol) and pyridine (0.98 ml, 12 mmol) in dry DCM (15 mL) at 0° C. under argon. After the addition, the mixture was warmed to ambient temperature and stirred for 24 hours. DCM (50 mL) was added, the solution was washed with H₂O (50 mL), 1 M aq. HCl (50 mL), saturated. aq. NaHCO₃ (50 ml), and brine (50 mL), dried (Na₂SO₄) and the solvent evaporated under reduced pressure. Purification of the residue by flash chromatography (silica gel, 4% MeOH/DCM) yielded the amide 21b (1.62 g, 58%) as a white solid.

Example 6—Synthesis of (6-((2-(sec-butyl)-1,3-dioxoisoindolin-4-yl)amino)-6-oxohexyl)triphenylphosphonium Bromide (Intermediate)

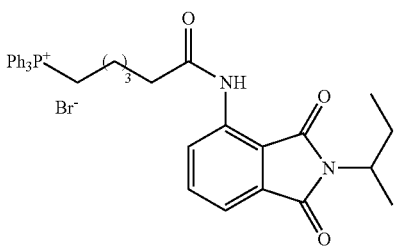

22a

A solution of 11a (429 mg, 1.09 mmol) and triphenylphosphine (570 mg, 2.17 mmol) in dry CH₃CN (15 mL) was refluxed for 72 hours. The mixture was concentrated in vacuo and the residue was purified by flash chromatography (10% MeOH/DCM) to afford the title compound 22a (362 mg, 51%) as a white solid.

Example 7—Synthesis of (6-((2-(sec-butyl)-1,3-dioxoisoindolin-4-yl)amino)-6-oxohexyl)tri-p-tolylphosphonium Bromide (Intermediate)

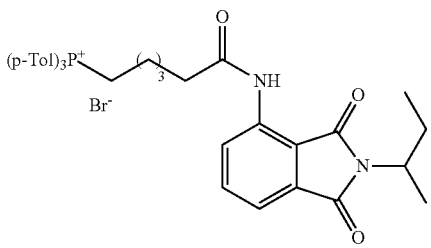

22b

A solution of 11a (146 mg, 0.37 mmol) and tri(p-tolyl)phosphine (225 mg, 0.74 mmol) in dry CH₃CN (6 mL) was refluxed for 72 hours. The mixture was concentrated in vacuo and the residue was purified by flash chromatography (7% MeOH/DCM) to afford the title compound 22b (256 mg, 99%) as a white solid.

Example 8—Synthesis of (11-((2-(sec-butyl)-1,3-dioxoisoindolin-4-yl)amino)-11-oxoundecyl)triphenylphosphonium Bromide (Intermediate)

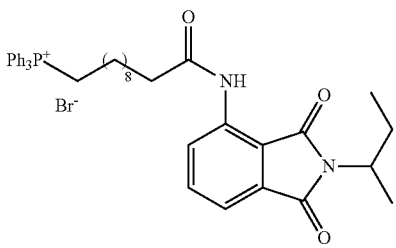

22c

A solution of 11b (400 mg, 0.86 mmol) and triphenylphosphine (678 mg, 2.58 mmol) in dry CH₃CN (5 mL) was refluxed for 72 h. The mixture was concentrated in vacuo and the residue was purified by flash chromatography (7% MeOH/DCM) to afford the title compound 22C (321 mg, 37%) as a white solid.

Example 9—Synthesis of (11-((2-(sec-butyl)-1,3-dioxoisoindolin-4-yl)amino)-11-oxoundecyl)tri-p-tolylphosphonium Bromide (Intermediate)

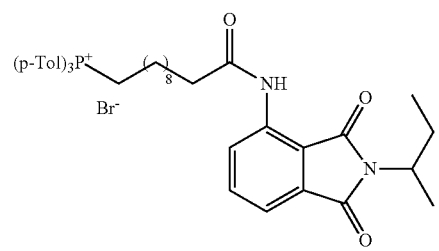

22d

A solution of 11b (400 mg, 0.86 mmol) and tri(p-tolyl)phosphine (785 mg, 2.58 mmol) in dry CH₃CN (7 mL) was refluxed for 72 hours. The mixture was concentrated in vacuo and the residue was purified by flash chromatography (50% MeOH/DCM) to afford the title compound 22d (636 mg, 96%) as a white solid.

Example 10—Synthesis of (11-((2-(sec-butyl)-1,3-dioxoisoindolin-4-yl)amino)-11-oxoundecyl)tricyclohexylphosphonium Bromide (Intermediate)

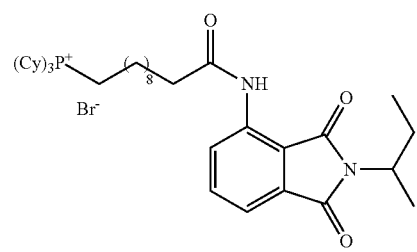

22e

A solution of 11b (400 mg, 0.86 mmol) and tricyclohexylphosphine (723 mg, 2.58 mmol) in dry CH₃CN (5 mL) was refluxed for 72 hours. The mixture was concentrated in vacuo and the residue was purified by flash chromatography (5% MeOH/DCM) to afford the title compound 22e (406 mg, 63%) as a white solid.

Example 11—Synthesis of (6-((2-(sec-butyl)-1,3-dioxoisoindolin-4-yl)amino)-6-oxohexyl)tri-p-tolylphosphonium Bromide (Intermediate)

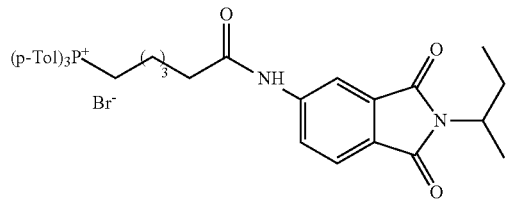

23a

A solution of 21a (350 mg, 0.89 mmol) and tri(p-tolyl)phosphine (539 mg, 1.77 mmol) in dry CH$_3$CN (4 mL) was refluxed for 72 hours. The mixture was concentrated in vacuo and the residue was purified by flash chromatography (5% MeOH/DCM) to afford the title compound 23a (448 mg, 72%) as a white solid.

Example 12—Synthesis of (6-((2-(sec-butyl)-1,3-dioxoisoindolin-5-yl)amino)-6-oxohexyl)tricyclohexylphosphonium Bromide (Intermediate)

23b

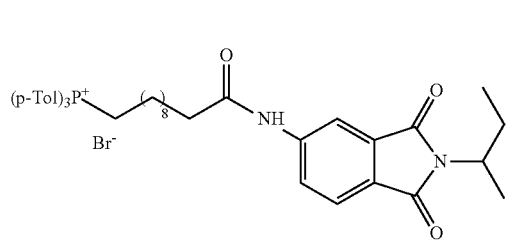

A solution of 21a (350 mg, 0.89 mmol) and tricyclohexylphosphine (497 mg, 1.77 mmol) in dry CH$_3$CN (4 mL) was refluxed for 72 hours. The mixture was concentrated in vacuo and the residue was purified by flash chromatography (5% MeOH/DCM) to afford the title compound 23b (529 mg, 88%) as a white solid.

Example 13—Synthesis of (11-((2-(sec-butyl)-1,3-dioxoisoindolin-5-yl)amino)-11-oxoundecyl)tri-p-tolylphosphonium Bromide (Intermediate)

23c

A solution of 21b (523 mg, 1.72 mmol) and tri(p-tolyl)phosphine (523 mg, 1.72 mmol) in dry CH$_3$CN (5 mL) was refluxed for 72 hours. The mixture was concentrated in vacuo and the residue was purified by flash chromatography (5% MeOH/DCM) to afford the title compound 23c (449 mg, 68%) as a white solid.

Example 14—Synthesis of Mitotropic 5-N-Acylated Luminol Derivatives 1a-e from Hydrazinolysis of the Respective Phthalimides 22a-e

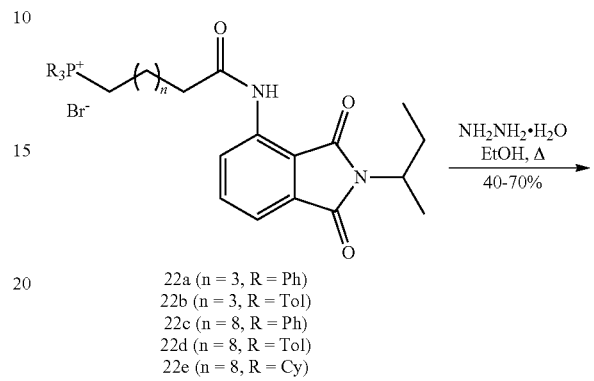

22a (n = 3, R = Ph)
22b (n = 3, R = Tol)
22c (n = 8, R = Ph)
22d (n = 8, R = Tol)
22e (n = 8, R = Cy)

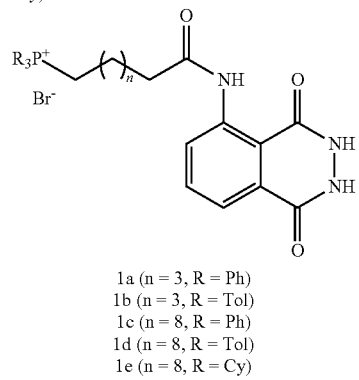

1a (n = 3, R = Ph)
1b (n = 3, R = Tol)
1c (n = 8, R = Ph)
1d (n = 8, R = Tol)
1e (n = 8, R = Cy)

Hydrazine hydrate (0.18 mL, 3.04 mmol) was added in a stirring solution of the given phthalimide (22a-e, 0.3 mmol) in absolute EtOH (6 mL) and the mixture was refluxed for 2 hours. The solvent was subsequently removed in vacuo and the residue was dissolved in H$_2$O (10 mL), acidified with 1 M aq. HC and extracted with DCM (3×30 mL). The combined organic layers were washed with brine, dried over Na$_2$SO$_4$, filtered and concentrated. The crude residue was purified by flash chromatography (5-15% MeOH/DCM) to afford the respective phthalhydrazide 1a (60%), 1b (32%), 1c (49%), 1d (60%) or 1e (30%) as a white solid.

Example 15—Synthesis of Mitotropic 6-N-Acylated Isoluminol Derivatives 2a-c from Hydrazinolysis of the Respective Phthalimides 23a-c

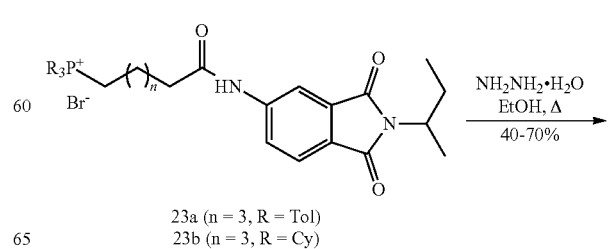

23a (n = 3, R = Tol)
23b (n = 3, R = Cy)
23c (n = 8, R = Tol)

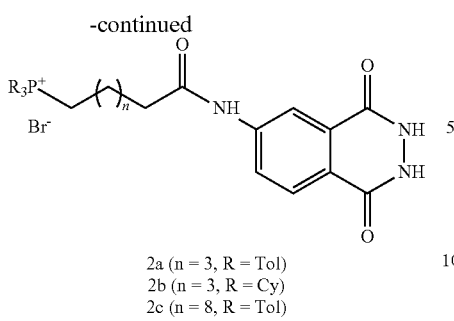

2a (n = 3, R = Tol)
2b (n = 3, R = Cy)
2c (n = 8, R = Tol)

Hydrazine hydrate (037 mL, 6.4 mmol) was added in a stirring solution of the given phthalimide (23a-c, 0.64 mmol) in absolute EtOH (15 mL) and the mixture was refluxed for 3 hours. The solvent was subsequently removed in vacuo and the residue was dissolved in $H_2O$ (20 mL), acidified with 1 M aq. HCl and extracted with DCM (3×50 mL). The combined organic layers were washed with brine, dried over $Na_2SO_1$ filtered and concentrated. The crude residue was purified by flash chromatography (15% MeOH/DCM) to afford the respective phthalhydrazide 2a (78%), 2b (62%) or 2c (37%) as a white solid.

Example 16—Synthesis of 1,2-bis-(2-iodoethoxy)ethane (Intermediate)

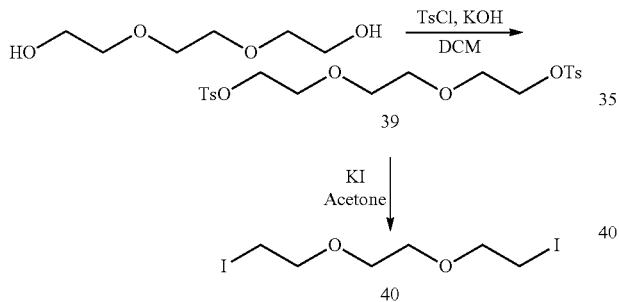

Step 1: Following a published procedure, triethylene glycol di-(P-toluenesulfonate) 39 was prepared (see Bonger et al., Bioorg. Med. Chem. 15: 4841-4856, 2007). Potassium hydroxide (3 g, 53.47 mmol) was added portion wise to a stirred solution of triethylene glycol (1 g, 6.66 mmol) and tosyl chloride (2.54 g, 13.32) in dry dichloromethane (25 mL) at 0° C. under argon and left stirring overnight at room temperature. DCM (25 mL) was then added, the mixture was poured onto ice/water, phases were separated, the aqueous phase washed with DCM (2×40 mL) and the combined organic layers were washed with water (40 mL) and dried ($Na_2SO_4$). Evaporation of the solvent left 39 (2.44 g, 80%) as white dust.

Step 2: Following a published procedure, 1,2-bis-(2-iodoethoxy)ethane 40 was prepared (see Lee et al., Bull. Korean Chem. Soc. 36: 1654, 2015). Sodium iodide (9.5 g, 0.06 mol) was added to a solution of tosylate 39 (10 g, 0.02 mmol) in acetone (150 mL) and the mixture was stirred at 60° C. overnight. The remaining precipitate was filtered off and the filtrate was concentrated to dryness. The residue was partitioned between DCM and water, the aqueous phase washed with DCM and the combined organic layer was washed with water, dried ($Na_2SO_4$) and concentrated to dryness, leaving 40 (6 g, 78%) as pale yellow solid.

Example 17—Synthesis of Phosphonium Iodides (Intermediates)

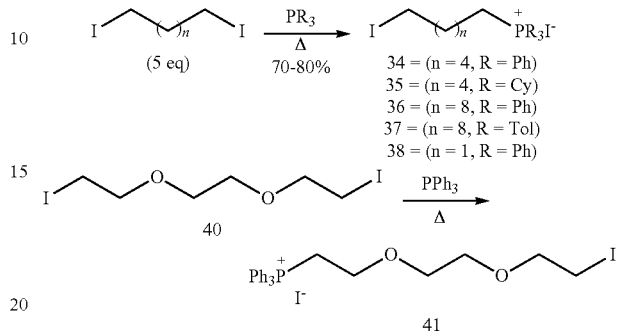

Following a published procedure (Lin et al., J. Biol. Chem. 277: 17048, 2002), the diiodo compound (5 mmol) and the respective phosphine (1 mmol) (diiodo-propane, -hexane, -decane or -1,2-bis(ethylenoxy)ethane 40) were mixed in a flask, heated at 100° C. and the resulting melt was stirred for 3 hours in the dark. After cooling, diethyl ether was added to the reaction mixture, the precipitate was filtered and washed with ether. The produce was re-dissolved in dichloromethane and precipitated again with the addition of ether, yielding the respective phosphonium iodide 34 (87%), 35 (45%), 36 (83%), 37 (60%), 38 (85%) or 41 (87%) as a brown solid.

Example 18—Synthesis of Mitotropic 5-N-Alkylated Luminol Derivatives 3a-f

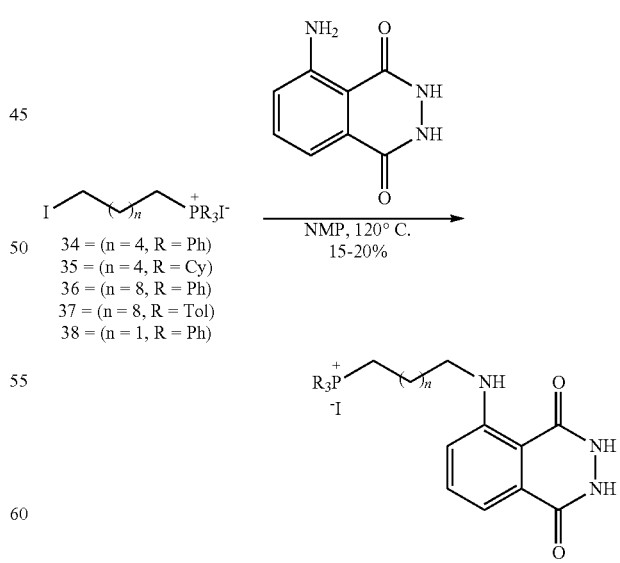

3a = (n = 4, R = Ph)
3b = (n = 4, R = Cy)
3c = (n = 8, R = Ph)
3d = (n = 8, R = Tol)
3d = (n = 1, R = Ph)

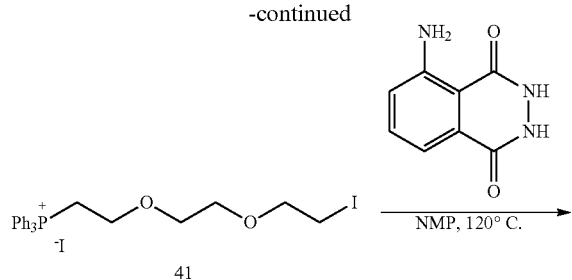

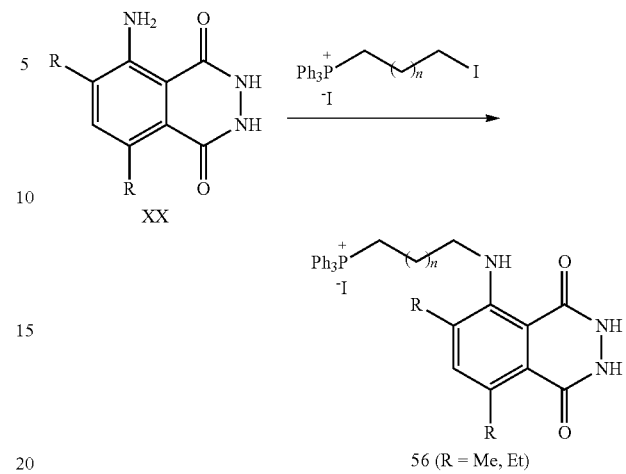

Example 19—Synthesis of Mitotropic Luminol Derivatives of General Structure 56

Compounds according to general structure 56 can be prepared by alkylation of known compounds of formula XX (see Griesbeck et al., Chem. Eur. J. 21: 9975, 2015) in a method analogous to the synthesis of compounds 3a-d.

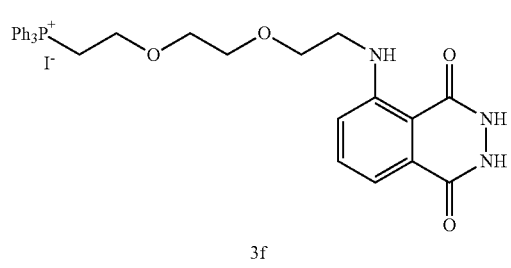

Luminol (400 mg, 2.26 mmol) was added to a solution of phosphonium iodide (34-38 or 41, 2.26 mmol) in N-methylpyrrolidone (2.5 mL) and the resulting solution was stirred at 110° C. for 24 hours. After cooling to room temperature, water (5 mL) was added and the precipitate thus formed was filtered and washed with aq. $Na_2S_2O_3$ and water. The residue was chromatographed (silica gel, DCM, EtOAc/DCM, MeOH/EtOAc/DCM, MeOH/DCM up to 40%), yielding pure 3a (24%), 3b (15%), 3c (25%), 3d (21%), 3e (20%) or 3f (3%).

Example 20—Synthesis of Mitotropic Luminol Derivatives of General Structure 57

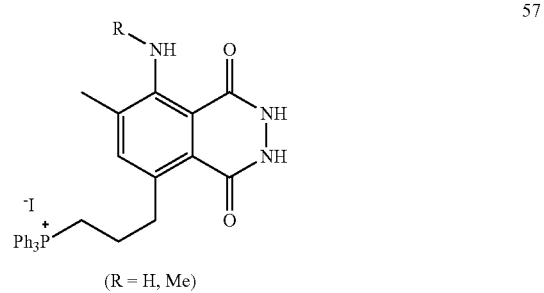

Compounds according to general structure 57 (R Me) can be prepared according to the following reaction scheme:

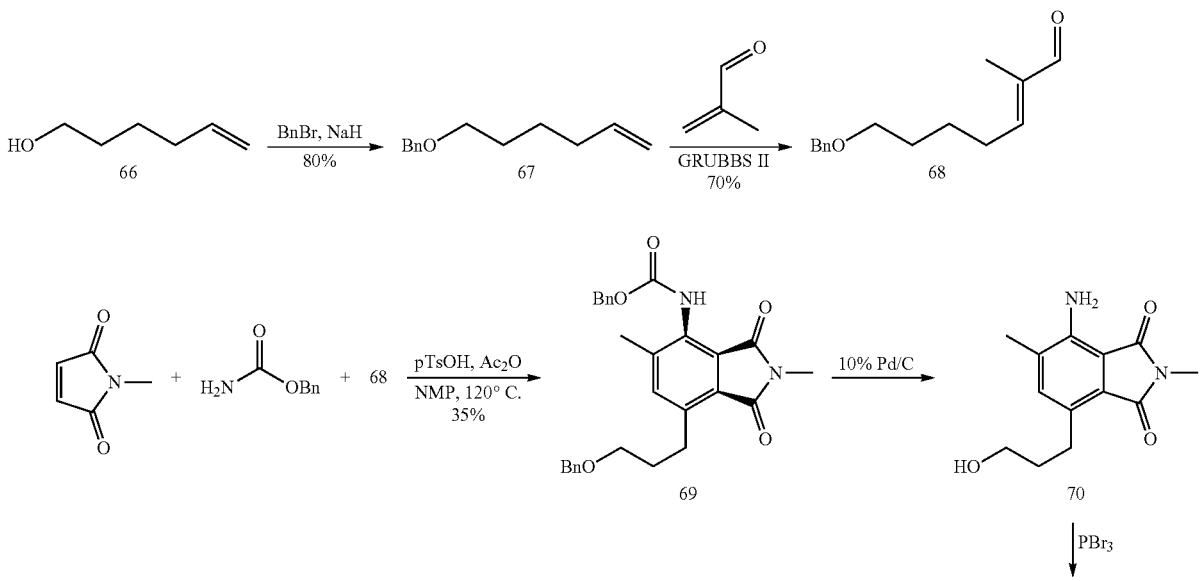

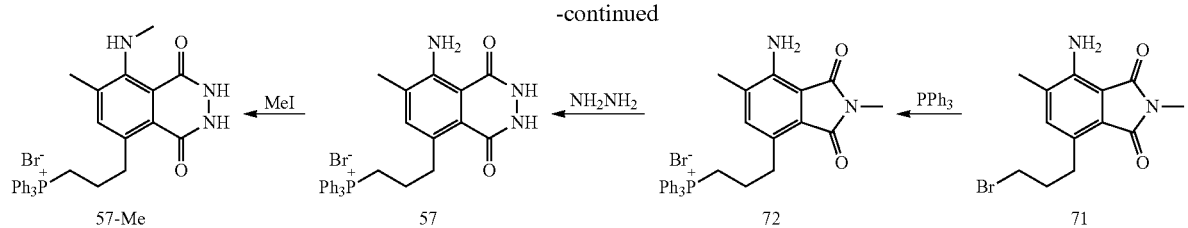

Example 21—Synthesis of Mitotropic Acridinium Ester Derivatives

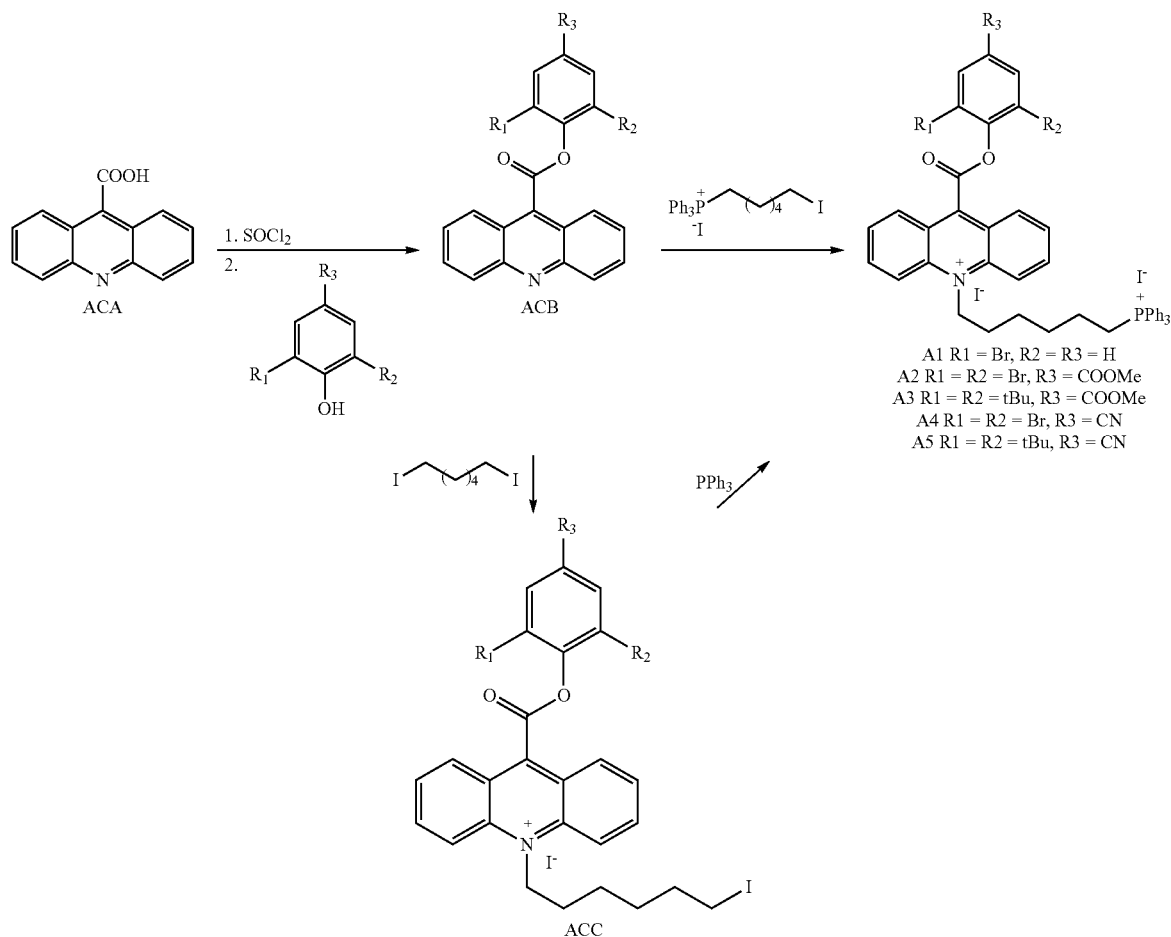

Mitotropic acridium ester derivatives A1-5 bearing a phosphonium moiety on an alkyl chain can be synthesised using a method similar to that used to prepare compounds 1-3. Starting from acridinic acid ACA, esterification is carried out using commercially available substituted phenols. This is followed by alkylation either directly to A1-5 (as in the synthesis of compounds 3), or via ACC (as in the synthesis of compounds 1 and 2).

Example 22—Synthesis of Mitotropic Acridinium Ester Derivatives

Mitotropic acridium ester derivatives B1-2 bearing a phosphonium moiety on an alkyl chain can be synthesised according to the following scheme:

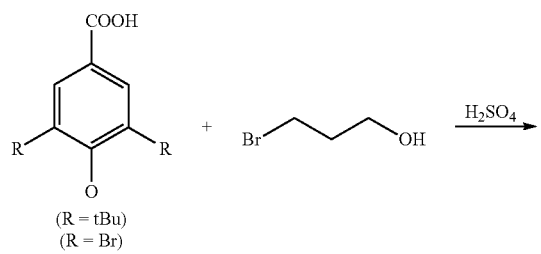
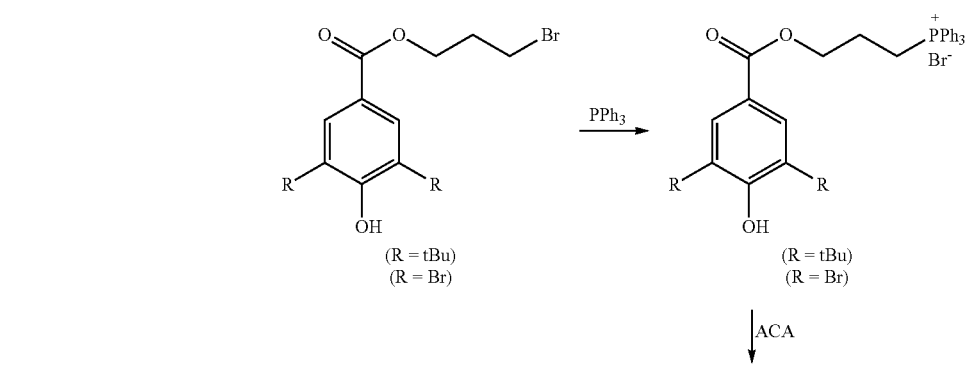
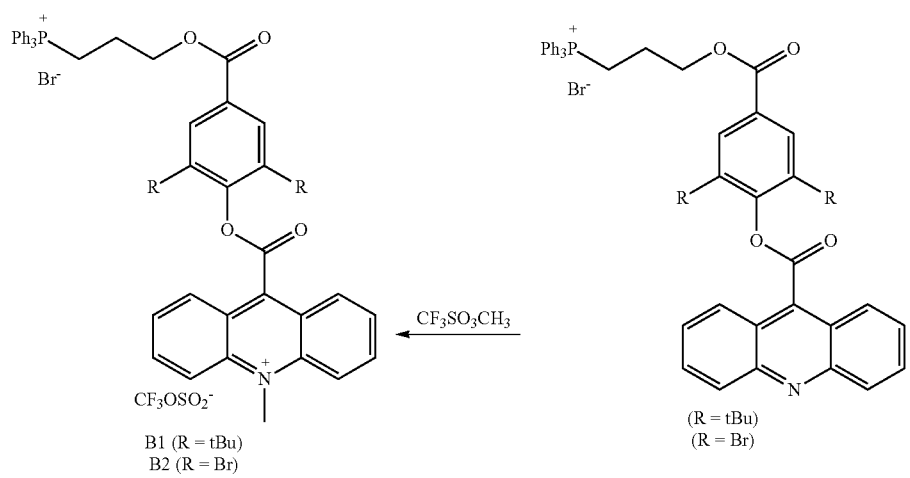
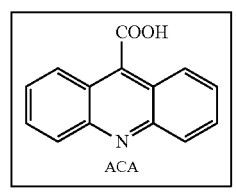
In this synthesis, the mitotropic chain is attached to the phenolic moiety, and the acridinium moiety is finally formed with methylation.

Example 23—Synthesis of a Luminol-Rhodamine Conjugate RLum

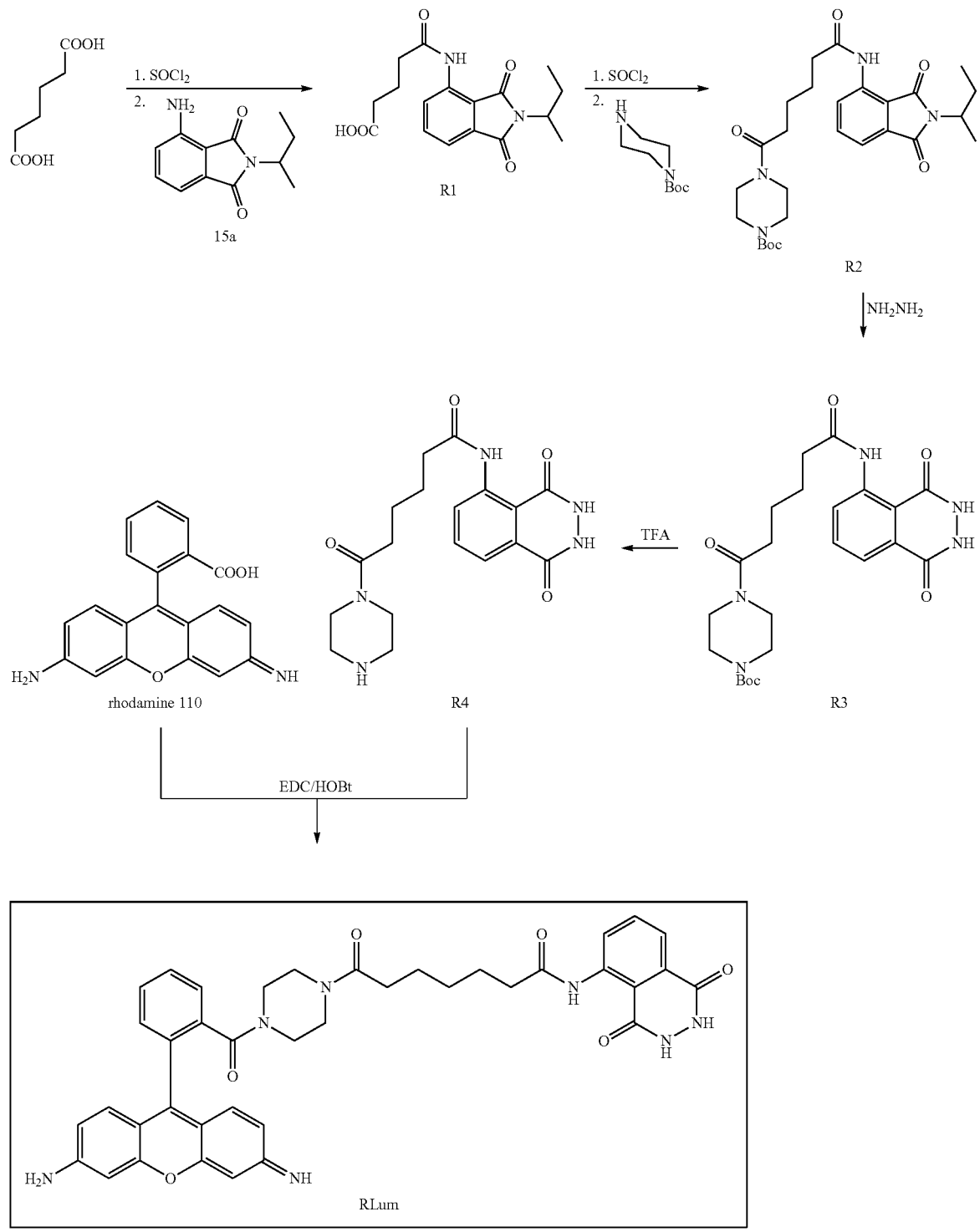

Excess adipic acid chloride is reacted with phthalimide 15a to yield acid R1 after aqueous work-up. R1 chloride is reacted with Boc-protected piperazine to form R2 which, after hydrazinolysis and subsequent hydrolysis, results in luminol derivative R4. This is then coupled with rhodamine 110 to yield the desired luminol-rhodium conjugate RLum.

Example 24—Synthesis of an
Acridinium-Rhodamine Conjugate RhAC
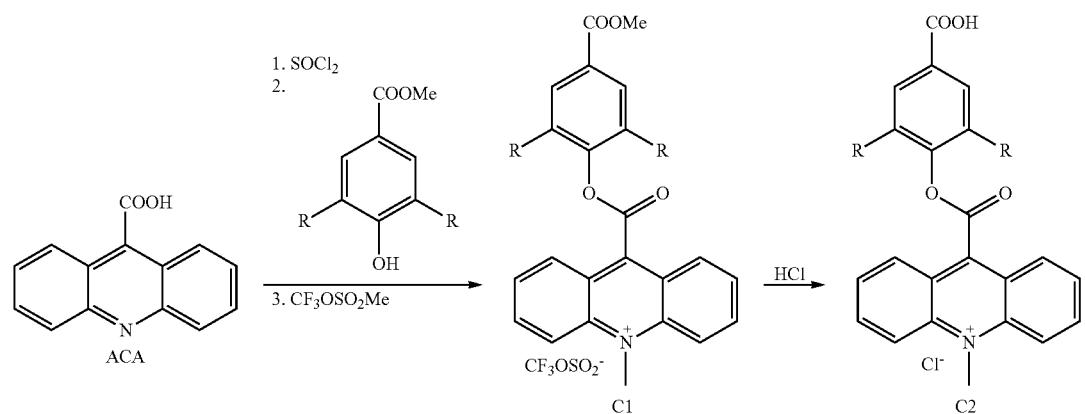
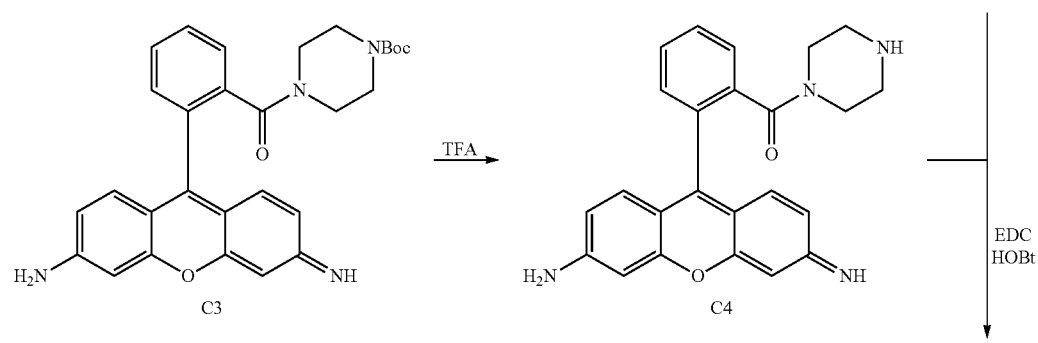
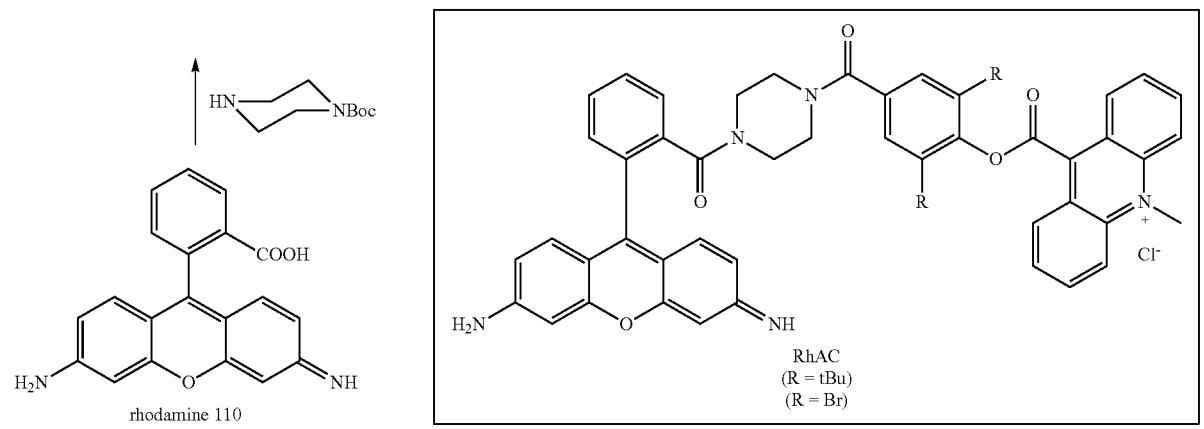

Acridinium ester C1 is prepared from ACA through coupling with a phenol and subsequent methylation. The carboxylic acid derivative C2 is prepared by hydrolysis of CI in a procedure similar to a published one (see Natrajan et al., RSC Adv., 4: 21852-21863, 2014). Rhodamine derivative C4 is prepared from rhodamine 110 through coupling with Boc-protected piperazine and subsequent hydrolysis.

C2 and C4 are coupled to yield the desired acridinium-rhodamine conjugate RhAC.

Examples 25 to 34

In Examples 25 to 34 the following codes are used to refer to the mitotropic conjugates according to the invention:

| Code | Compound Number | Chemical Structure |
|------|-----------------|--------------------|
| AP47 | 1a | 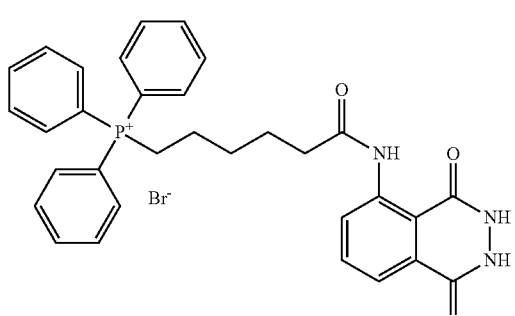 |

Molecular Weight: 616.50
(6-((1,4-dioxo-1,2,3,4-tetrahydrophthalazin-5-yl)amino)-6-oxohexyl)triphenylphosphonium bromide

| | | |
|------|-----|---|
| AP52 | 1b | 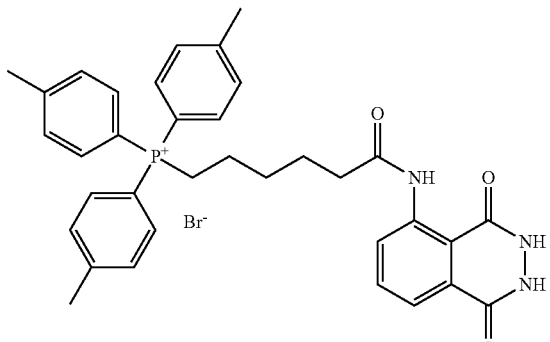 |

Molecular Weight: 658.58
(6-((1,4-dioxo-1,2,3,4-tetrahydrophthalazin-5-yl)amino)-6-oxohexyl)tri-p-tolylphosphonium bromide

| | | |
|------|-----|---|
| AP53 | 1c | 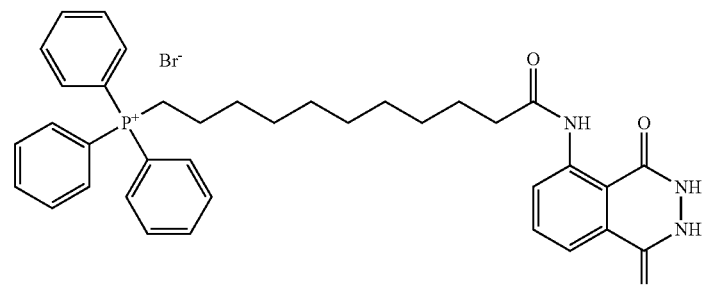 |

Molecular Weight: 686.63
(11-((1,4-dioxo-1,2,3,4-tetrahydrophthalazin-5-yl)amino)-11-oxoundecyl)triphenylphosphonium bromide

| Code | Compound Number | Chemical Structure |
|---|---|---|
| AP54 | 1d | 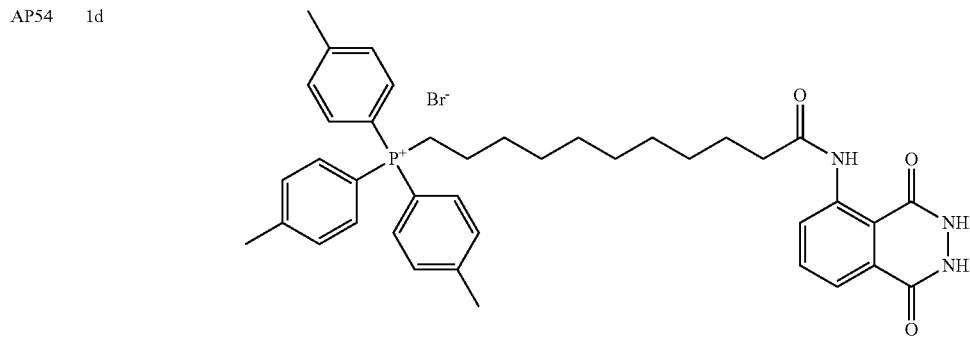<br>Molecular Weight: 728.71<br>(11-((1,4-dioxo-1,2,3,4-tetrahydrophthalazin-5-yl)amino-<br>11-oxoundecyl)tri-p-tolylphosphonium bromide |
| AP55 | 1e | 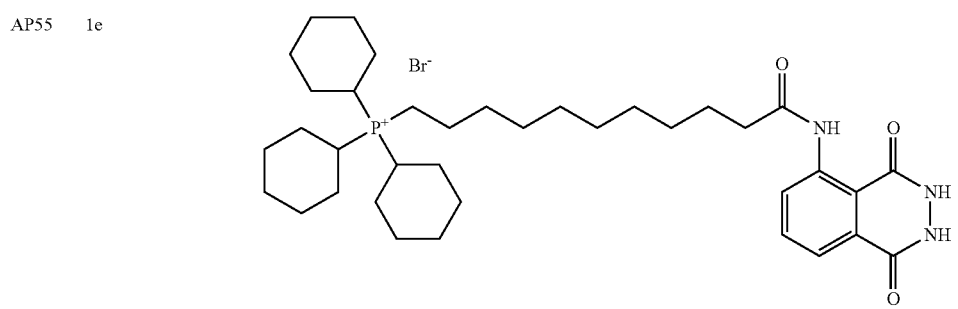<br>Molecular Weight: 704.77<br>tricyclohexyl(11-((1,4-dioxo-1,2,3,4-tetrahydrophthalazin-<br>5-yl)amino)-11-oxoundecyl)phosphonium bromide |
| AP71 | 2c | 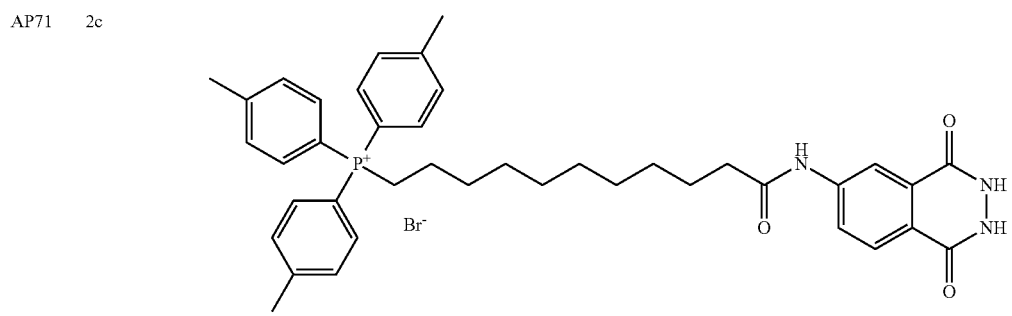<br>Molecular Weight: 728.71<br>(11-((1,4-dioxo-1,2,3,4-tetrahydrophthalazin-6-yl)amino)-<br>11-oxoundecyl)tri-p-tolylphosphonium bromide |

-continued

| Code | Compound Number | Chemical Structure |
|---|---|---|
| AP72 | 2a | 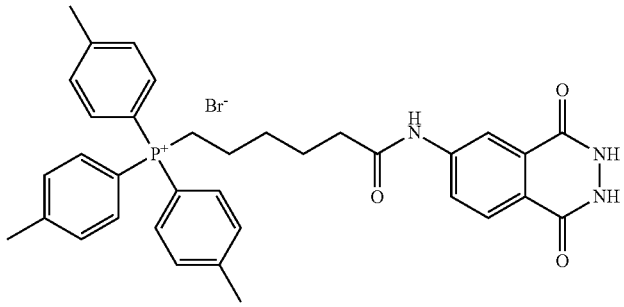 [SMILES: Cc1ccc([P+](CCCCCC(=O)Nc2ccc3c(=O)[nH][nH]c(=O)c3c2)(c2ccc(C)cc2)c2ccc(C)cc2)cc1 ; [Br-]]<br>Molecular Weight: 658.58<br>(6-((1,4-dioxo-1,2,3,4-tetrahydrophthalazin-6-yl)amino-6-oxohexyl)tri-p-tolylphosphonium bromide |
| AP74 | 2b | 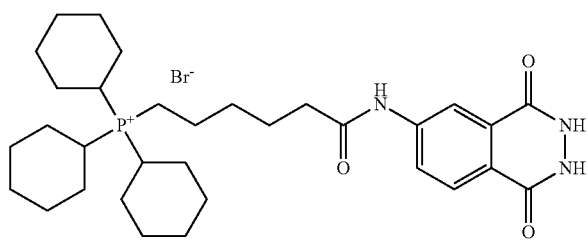 [SMILES: O=C(CCCCC[P+](C1CCCCC1)(C1CCCCC1)C1CCCCC1)Nc1ccc2c(=O)[nH][nH]c(=O)c2c1 ; [Br-]]<br>Molecular Weight: 634.64<br>tricyclohexyl(6-((1,4-dioxo-1,2,3,4-tetrahydrophthalazin-6-yl)amino)-6-oxohexyl)phosphonium bromide |
| DZ163 | 3d | 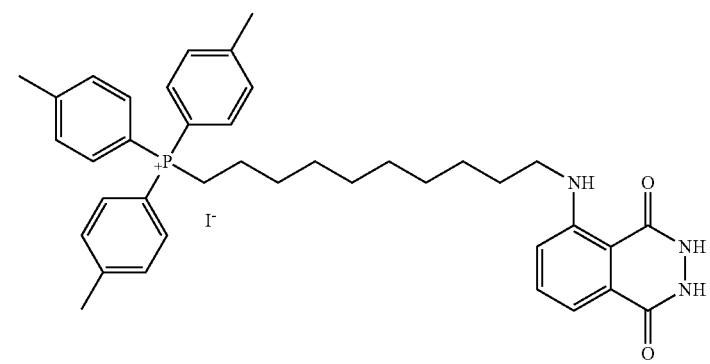 [SMILES: Cc1ccc([P+](CCCCCCCCCCNc2cccc3c(=O)[nH][nH]c(=O)c23)(c2ccc(C)cc2)c2ccc(C)cc2)cc1 ; [I-]]<br>Molecular weight: 747.70<br>(10-((1,4-dioxo-1,2,3,4-tetrahydrophthalazin-5-yl)amino)decyl)tri-p-tolylphosphonium iodide |
| DZ160 | 3b | 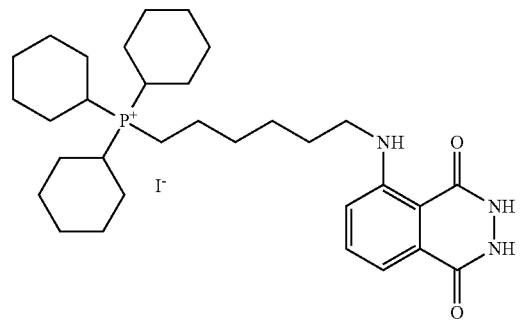 [SMILES: O=c1[nH][nH]c(=O)c2c(NCCCCCC[P+](C3CCCCC3)(C3CCCCC3)C3CCCCC3)cccc12 ; [I-]]<br>Molecular Weight: 667.66<br>tricyclohexyl(6-((1,4-dioxo-1,2,3,4-tetrahydrophthalazin-5-yl)amino)hexyl)phosphonium iodide |

-continued

| Code | Compound Number | Chemical Structure |
|---|---|---|
| DZ167 | 3a | 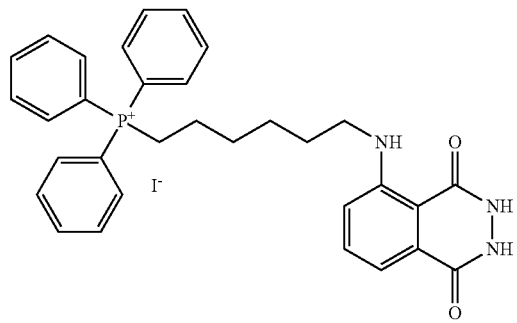 [SMILES: O=c1[nH][nH]c(=O)c2c(NCCCCCC[P+](c3ccccc3)(c3ccccc3)c3ccccc3)cccc12 ; [I-]]<br>Molecular Weight: 649.51<br>(6-((1,4-dioxo-1,2,3,4-tetrahydrophthalazin-5-yl)amino)hexyl)triphenylphosphonium iodide |
| DZ168 | 3c | 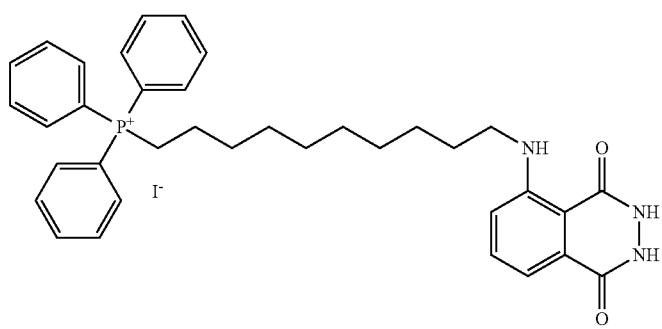 [SMILES: O=c1[nH][nH]c(=O)c2c(NCCCCCCCCCC[P+](c3ccccc3)(c3ccccc3)c3ccccc3)cccc12 ; [I-]]<br>Molecular Weight: 705.62<br>(10-((1,4-dioxo-1,2,3,4-tetrahydrophthalazin-5-yl)amino)decyl)triphenylphosphonium iodide |
| DZ203 | 3e | 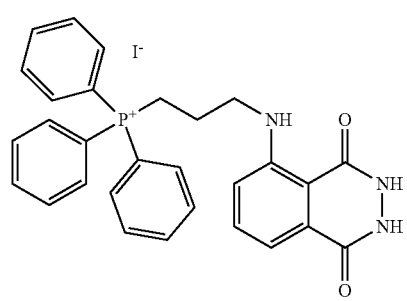 [SMILES: O=c1[nH][nH]c(=O)c2c(NCCC[P+](c3ccccc3)(c3ccccc3)c3ccccc3)cccc12 ; [I-]]<br>Molecular Weight: 607.43<br>(3-((1,4-dioxo-1,2,3,4-tetrahydrophthalazin-5-yl)amino)propyl)triphenylphosphonium iodide |

| Code | Compound Number | Chemical Structure |
|---|---|---|
| DZ196 | 3f | Molecular Weight: 681.51<br>(2-(2-(2-((1,4-dioxo-1,2,3,4-tetrahydrophthalazin-5-yl)amino)ethoxy)ethoxy)ethyl)triphenylphosphonium iodide |

Example 25—Luminescence of Mitotropic Luminol Derivatives in Conditions Resembling the Mitochondrial Matrix Luminescence of the mitotropic luminol derivatives was investigated in biomimetic conditions mimicking those found in the mitochondrial matrix environment. The high protein content of the mitochondrial matrix and the abundance of hemes and metal-containing enzymes was represented in the model by 10% Fetal Bovine Serum (FBS).

Tris buffer (200 μL, 50 mM) set to pH 7.9 was added to a test tube for use in the ABEL meter (portable luminescence meter available from Knight Scientific). This was then supplemented with 10% Fetal Bovine Serum (FBS). Each compound to be investigated was added at 100 mM, followed by urea-$H_2O_2$ (10 mM). After the initial steady-state profile of the luminescence was obtained, $CuSO_4$ was injected in real time at 2 mM. The results are presented in FIG. 2.

Example 26—Luminescence of Mitotropic Luminol Derivatives in MCF7 Cells

Chemiluminescence from MCF7 cells was recorded upon application of various luminol derivatives. In order to achieve this, three strategies were followed: 1) compounds dissolved in DMSO were applied to a monolayer of cells (~5 million) pelleted at the U-shaped bottom of the luminometer test-tube; 2) compounds dissolved in propylene glycol and applied to the same cell monolayers as above; and 3) compounds dissolved in DMSO and applied to a cell concentrate (5 million cells) in 200 μl of PBS. A characteristic example of the experimental results is provided in FIG. 3 for DZ163 (compound 3d).

Cells were grown in a T175 flask and grown to confluence. The cells were then detached by trypsin, centrifuged into a big pellet and re-suspended in 12 ml medium (RPMI 1640 without phenol red). 1 mL of this suspension was introduced into each of 12 flow cytometry tubes and these were centrifuged so that the cells formed a film at their U-shaped bottoms. The tubes were placed in the ABEL meter and scanned. The luminol moiety (100 μM in propylene glycol) was then added and finally, where necessary, DMSO was injected in real time.

In all cases, the luminescence in the cell layer was only induced by the introduction of DMSO, either as a solvent of the luminol derivatives or as a subsequent additive. No additional oxidants such as hydrogen peroxide or any catalysts such as metals were used. It has to be noted that pure DMSO will eventually kill the cells but luminescence registration was instantaneous (seconds after injection). Even in the eventuality of cell death, however, DMSO facilitated the luminescence of the mitotropic compounds. The level of luminescence was substantially decreased in the dispersed cells, most probably due to increased volume.

Example 27—Energy Transfer Between Luminol Luminescence and Various Photosensitizers The feasibility of energy transfer from luminescent luminol to various photosensitizers was investigated. The chemiluminescence emission profiles were recorded with the use of a Horiba iHR320 f/4.1 imaging spectrometer equipped with a Synapse CCD head. The emission of luminol (100 μM) was excited in DMSO, with the addition of base (either KOH or potassium tert.butoxide, 100 mM) and the photosensitizers were added. In the case of TPPS4 which was dissolved in water, luminol luminescence was excited by the addition of urea-$H_2O_2$ (10 mM) and catalyst ($CuSO_4$ at 2 mM). The singlet oxygen registration was facilitated by the use of a Hamamatsu 5509-73 NIR PMT detector. Two filters were placed in front of the detector—a long-pass filter with a cut on at ~1000 nm and a bandpass filter centred at 1270 nm, which is the central wavelength of singlet oxygen phosphoresence. The results are presented in FIGS. 4 and 5.

FIG. 4 shows the energy transfer between luminol luminescence and various photosensitisers: A) luminescence of luminol in alkaline DMSO (KOH); B) addition of hypocrellin A (HYPA)—the characteristic HYPA fluorescence can be seen (around 600 nm); C) addition of hypericin (HYP) instead of HYPA—again the characteristic HYP fluorescence double peak at 600 and 650 can be seen; D) luminol in aqueous carbonate buffer (pH 10.3) with the addition of $CuSO_4$ and urea peroxide in the presence of Rose Bengal (RB)—the characteristic fluorescence of RB is obvious as verified in E) by 532 nm laser excitation; and F) the luminol system in carbonate buffer as in D) but with the addition of TPPS4, a porphyrin spectrally similar to 5-ALA-derived PpIX—the characteristic fluorescence of TPPS4 is not present. Luminol emission in the aqueous system shows a hump at around 400 nm in addition to the main peak around 490 nm. In the presence of TPPS4 (F) this hump is severely depleted which shows that TPPS4 absorbs strongly at this region in contrast to the other photosensitizers which seem to deplete the main peak at 490 nm.

In FIG. 5, the photosensitiser erythrosin B is added to luminol in DMSO alkalinised by potassium tert.butoxide.: A) the spectrum of luminol in DMSO-tert-butoxide; B) erythrosin B absorbs very strongly, especially around 500 and demonstrates very strong fluorescence around 580 nm; and C) addition of tert.butoxide to the DMSO-luminol solution triggered strong and long-lived luminol luminescence and also luminescence around 1270 nm indicating the presence of singlet oxygen since this luminescence was quenched by histidine.

These experiments demonstrate that many photosensitizers can receive energy from luminol luminescence.

Example 28—Micrographs of Luminol Derivatives and Luminol

The sub-cellular localisation of the luminol derivatives was investigated. Cells were inoculated into Petri dishes with glass bottoms and left to grow overnight. The cells were treated with the luminol moieties for 4 hours and then 15 mins prior to imaging, mitotracker green FM was added (100 nm). The cells were washed with PBS and mounted onto a Zeiss LSM 710 confocal microscope. The luminol fluorescence was excited at 405 nm, while the mitotracker green FM fluorescence was excited at 488 nm. The luminol emission was collected between 420-490 nm (red channel) while the mitotracker green FM fluorescence was collected at the FITC channel (green channel). The green and red channel images were subsequently superimposed in Photoshop to yield the overlay images. In these images, yellow in each case indicated co-localisation of the luminol derivative with mitotracker green FM (and hence with cell mitochondria).

The representative micrographs in FIG. 6 give an overview of the subcellular localisation of the mitotropic compounds versus that of free luminol. On the triple column (left) the mitochondrial localisation of two derivatives namely DZ160 and AP47 is shown in two different cell lines, the breast adenocarcinoma cell line MCF7 and the glioblastoma cell line U87. The three micrographs in each row of this triple column depict the localisation of the derivative, the localisation of the mitochondrial marker mitotracker green and the overlay of these two localisations in a merged image. The fluorescence of luminol is represented in the left column while mitotracker green fluorescence is shown in the middle column. Their overlay is shown in the third column. On the column in the right (fourth column) the cytosolic localisation of free luminol is shown on the top (with border) while in two cases the localisation of AP47 and DZ160 is depicted in cells not incubated with mitotracker green to exclude fluorescence spillover and hence cross talk between the mitotracker and luminol-derivative channels. This confirms the dissimilar localisation of the luminal derivatives (mitochondria) and free luminol (cytosolic).

Example 29—5-ALA/Hypocrellin A and HD92 (AP47) on U87 and MCF7 Cells

Efficiency of the luminol derivatives was investigated. The initial derivative tested was HD92 (also referred to herein as "AP47"). U87 cells were inoculated in 96 well plates. The cells were then divided into the following groups (at least 6 parallels per group): CTRL (media only), ALA CTRL (2 mM), HD92 CTRL (500 µM) and the LUMIBLAST group (2 mM 5-ALA and 500 µM HD92). Correspondingly, MCF7 cells were inoculated in 96 well plates and left to grow overnight. The cells were then divided into the following groups (at least 6 parallels per group): CTRL (media only), Hypocrellin A CTRL (HYPA 7 µM), HD92 CTRL (500 µM) and the LUMIBLAST group (7 µM HYPA and 500 µM HD92). These four groups were incubated in media with and without 10 µM $FeSO_4$ in the case of experiments with HYPA. Following incubation of the cells with their respective drug strategies overnight (~20 hours), the cell groups were tested for their viability using a standard MTT assay. In brief, all cell groups were incubated with 0.5 mg/mL MTT for 3 hours. The MTT media were subsequently replaced with DMSO (100 µL) to solubilise the formazan. The wells were read for absorbance at 562 nm using a Tecan Spark OM plate reader. The cytotoxicity was determined as the percentage of control (media only) absorbance following subtraction of blank values from wells without cells.

The results are presented in FIG. 7. From the data obtained it can be seen that these results were obtained at very high concentrations of HD92, still sub-toxic but very near the margins of chemical toxicity. It can also be seen that 5-ALA is less efficient in producing LUMIBLAST effects than HYPA as a photosensitizer, however, the HYPA effects were achieved in the presence of metal catalyst, in the present case small concentration of $FeSO_4$. The data also shows that since the combined experimental group survival values are shown with respect to the HD92 (LTPP1) control, the combinatory cytotoxic effect is profoundly significant and a result of photosensitizer (PS) and HD92 synergy.

Example 30—HYPA, DZ168 and $CuSO_4$ in MCF7 and U87 Cells

MCF7 and U87 cells were inoculated in 96 well plates. The cells were then divided into the following groups (at least 6 parallels per group): CTRL (media only), HYPA CTRL (3 µM), DZ168 CTRL (5, 10, 20 and 30 µM), and the LUMIBLAST combinations (3 µM HYPA+DZ168 5-30 µM). These cell group incubations were also repeated in media containing 100 µM $CuSO_4$. Following incubation of the cells with their respective drug strategies overnight (~20 hours), the cell groups were tested for their viability using the MTT assay.

The results are presented in FIG. 8. When HYPA was employed as the photosensitizer, MCF7 cells showed enhanced toxicity in the HYPA+copper groups, while the U87 cell groups were not affected.

Example 31—HYPA, DZ167 and $CuSO_4$ in MCF7 and U87 Cells

MCF7 and U87 cells were inoculated in 96 well plates. The cells were then divided into the following groups (at least 6 parallels per group):CTRL (media only), HYPA CTRL (5 µM), DZ167 CTRL (25-200 µM), and the LUMIBLAST combinations (5 µM HYPA+DZ167 25-200 µM). These incubations were performed in media containing 50 µM $CuSO_4$. Following incubation of the cells with their respective drug strategies overnight (~20 hours), the cell groups were tested for their viability using the MTT assay.

The results are presented in FIG. 9. At 200 μM concentration of DZ167, 5 μM HYPA and 50 μM CuSO₄, there is a synergistic effect in U87 cells.

Example 32—Sub-Cellular Localisation of Cercosporin and Erythrocin B in T98G Glioblastoma Multiforme Cells The subcellular localisation of cercosporin together with that of Erythrosin B was investigated. Cells were inoculated into Petri dishes with glass bottoms and left to grow overnight. The cells were treated with Erythrosin B (4 μM) and cercosporin (3 μM) for 4 hours and then 15 mins prior to imaging, mitotracker deep-red FM was added (100 nm). The cells were washed with PBS and mounted onto a Zeiss LSM 710 confocal microscope. The cercosporin and erythrosin B fluorescence was excited at 488 nm, while the mitotracker deep-red FM fluorescence was excited at 633 nm. The cercosporin and erythrosin B emission was collected emission was collected beyond 550 nm (green channel) while the mitotracker deep-red FM fluorescence was collected beyond 640 nm (red channel). The green and red channel images were subsequently superimposed in Photoshop to yield the overlay images. In these images, yellow in each case indicates co-localisation of the photosensitizers with mitotracker green FM (and hence cell mitochondria). From the micrographs in FIG. 10 it can be seen that cercosporin and erythrocin B partly co-localise with cell mitochondria and hence they can be used in LUMIBLAST.

Example 33—Cercosporin and DZ203/DZ196 in U87 GBM Cells

The subcellular localisation of cercosporin together with that of synthesised derivatives DZ203 (short alkyl linker) and DZ196 (oligoPEG linker) was investigated. U87 cells were inoculated in 96 well plates. The cells were then divided into the following groups (at least 6 parallels per group). CTRL (media only), Cercosporin CTRL (3 μM), DZ203 CTRL (200 μM), DZ196 CTRL (500 μM) and the LUMIBLAST combinations (3 μM cercosporin+DZ203 200 μM or 3 μM cercosporin DZ196 500 μM). These incubations were performed in media with and without 100 μM CuSO₄. Following incubation of the cells with their respective drug strategies overnight (20 hours), the cell groups were tested for their viability using the MTT assay. The results are presented in FIG. 11 and show a very profound effect for cercosporin incubated with DZ203 (200 μM) for 24 hours in the presence of Cu (150 μM). The smaller effect with DZ196 (500 μM) was achieved without the catalytic effect of Cu.

Example 33—Metabolic Analysis of MCF7 Cells with DZ167 and 5-ALA

Metabolic analysis was performed to investigate the respiration and glycolysis of intact cells upon administration of the luminol derivatives and photosensitizer (exemplified here by AP47 and 5-ALA respectively). MCF7 cells were inoculated into XFe96 seahorse metabolic analyser 96-well plates and left overnight to incubate. The cells were incubated in un-buffered medium without FBS at a 37° C. incubator without $CO_2$ for one hour prior to the experiments. The cells were then analysed for their oxygen consumption rates (OCR) corresponding to respiratory activity and extracellular acidification rates (ECAR) corresponding to the glycolytic activity of the cells. The measurements were then performed with the help of the XFe96 metabolic analyser, at 4 conditions (serial injections) as denoted on the graphs in FIG. 12. These injections included the luminol mitotropic derivative AP47 (200 μM) and 5-ALA (1 mM) to study their effect and the effect of their combination on the cellular metabolism. Also oligomycin (1 μM), FCCP (1 μM), and a combination of Antimycin A and Rotenone (1 μM each), were used to modulate the cellular respiration. Oligomycin inhibits ATP synthesis revealing the amount of respiration required for ATP production, FCCP collapses the mitochondrial proton gradient forcing maximal electron transport and hence maximal oxygen consumption. Finally, the mix of rotenone and antimycin A totally inhibits the electron transport to the mitochondrial complex III stopping all respiratory activity. In some instances, also 2-deoxy glucose (2DG) was also injected to the cells as it totally inhibits cell glycolysis, as a tool to study the effects of AP47 and 5-ALA on cell glycolysis.

Example 34—5-ALA and DZ203 in MDA-MB-231 Breast Carcinoma Cells

MDA-MB-231 cells were inoculated in 96 well plates. The cells were then divided into the following groups (at least 6 parallels per group): CTRL (media only), 5-ALA CTRL (1.2 mM), DZ203 CTRL (400 μM) and the LUMIBLAST combinations (1.2 mM 5-ALA+DZ203 400 μM). These incubations were performed in media in the presence and absence of a catalyst (100 μM CuSO₄). Following incubation of the cells with their respective drug strategies overnight (~20 hours), the cell groups were tested for their viability using the MTT assay. The results are presented in FIG. 13 and show a substantial synergy in the presence of Cu as catalyst.

The invention claimed is:
1. A method of photodynamic therapy of cells or tissues of a patient, said method comprising administering to said cells or tissues an effective amount of a mitochondria-targeted chemiluminescent agent which is a conjugate comprising a chemiluminescent moiety attached to a mitotropic moiety and, simultaneously, separately, or sequentially thereto, an effective amount of a photosensitizer or a precursor thereof:
wherein said agent is a compound of formula (III), or a pharmaceutically acceptable salt thereof:

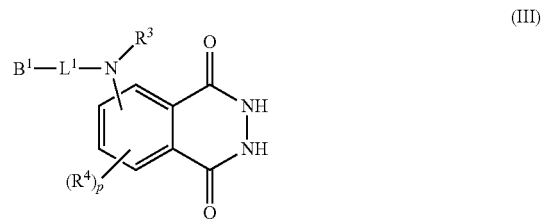

(III)

where $L^1$ is a linker;
$B^1$ is a mitotropic moiety which is the following group:

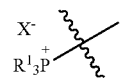

where $R^1$ is phenyl, toluene, or cyclohexyl; and X is a monovalent anion;

$R^3$ is hydrogen, or an alkyl group;

each $R^4$ is independently selected from $C_{1-6}$ alkyl, and $-NR^5R^6$;

$R^5$ and $R^6$ are independently selected from H and $C_{1-6}$ alkyl; and p is an integer from 0 to 3.

2. The method as claimed in claim 1, wherein said agent is a compound of formula (IIIa) or (IIIb):

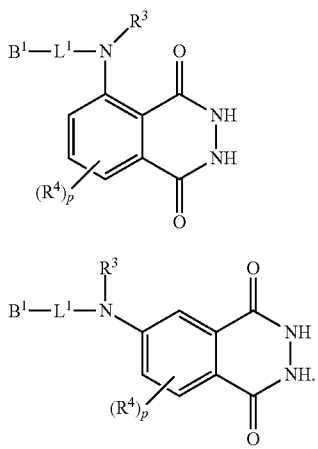

3. The method as claimed in claim 1, wherein $L^1$ is selected from the group consisting of:

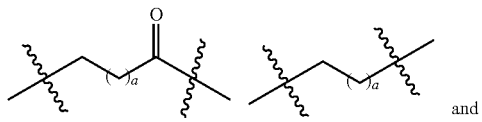

(where a is an integer from 1 to 10; and b is an integer from 1 to 4).

4. The method as claimed in claim 1, wherein said photosensitizer or precursor is selected from 5-aminolevulinic acid (5-ALA) and derivatives of 5-ALA, protoporphyrins; phthalocyanines; sulphonated tetraphenylporphyrins; chlorins; chlorin derivatives; mono-L-aspartyl chlorin e6 (NPe6) or chlorin e6; natural and synthetic porphyrins; anthraquinones and derivatives thereof.

5. The method as claimed in claim 4, wherein said photosensitizer precursor is 5-aminolevulinic acid (5-ALA), a derivative or pharmaceutically acceptable salt thereof.

6. The method as claimed in claim 1 for the photodynamic treatment of any disorder or abnormality of cells or tissues in an animal body which are responsive to photodynamic therapy.

7. The method as claimed in claim 6 for the treatment of cancer.

8. The method as claimed in claim 7, wherein said cancer is selected from the group consisting of gliomas and other brain cancers, hepatic and pancreatic cancers, breast, lung and prostate cancer, cholangiocarcinoma, stomach and colon cancers, bladder cancer, cervical cancers, head and neck cancers.

9. The method as claimed in claim 8, wherein said cancer is GBM.

* * * * *